United States Patent [19]

Dejter, Jr. et al.

[11] Patent Number: 5,060,658

[45] Date of Patent: Oct. 29, 1991

[54] FINE-NEEDLE ASPIRATION CELL SAMPLING APPARATUS

[75] Inventors: Stephen W. Dejter, Jr., Washington, D.C.; Richard H. Goodwin, Jr., Bethesda, Md.

[73] Assignee: Vance Products Incorporated, Spencer, Ind.

[21] Appl. No.: 559,260

[22] Filed: Jul. 30, 1990

Related U.S. Application Data

[63] Continuation of Ser. No. 159,320, Feb. 23, 1988, Pat. No. 4,989,614.

[51] Int. Cl.⁵ ............................................. A61B 10/00
[52] U.S. Cl. .................................... 128/753; 606/171
[58] Field of Search ......................... 128/749-754; 606/167, 170, 171, 172

[56] References Cited

U.S. PATENT DOCUMENTS

| | | | |
|---|---|---|---|
| 2,516,492 | 7/1950 | Turkel | 128/751 |
| 3,995,619 | 12/1976 | Glatzer | 128/754 |
| 4,142,517 | 3/1979 | Stavropoulos et al. | 128/754 |
| 4,600,014 | 7/1986 | Beraha | 128/754 |
| 4,681,123 | 7/1987 | Valtchev | 128/753 |
| 4,699,154 | 10/1987 | Lindgren | 128/754 |
| 4,763,667 | 8/1988 | Manzo | 128/750 |
| 4,819,635 | 4/1989 | Shapiro | 128/752 |
| 4,881,551 | 11/1989 | Taylor | 128/754 |
| 4,909,249 | 3/1990 | Akkas et al. | 128/753 |

*Primary Examiner*—Max Hindenburg
*Attorney, Agent, or Firm*—Woodard, Emhardt, Naughton, Moriarty & McNett

[57] ABSTRACT

Apparatus and methods for performing fine-needle aspiration biopsies are disclosed. Each method and apparatus includes a needle having an opening which can be occluded during both the penetration and withdrawal stages of the aspiration cycle. After penetration of the target area, the needle is reciprocated a predetermined number of times determined by the desired cytological sample yield. The needle is unoccluded during the reciprocation phase of the cycle. Both manual and automatic apparatus for performing the fine-needle aspiration biopsy procedures in accordance with the disclosed method are disclosed. Numerous sheath configurations for various biopsy applications are illustrated, including those applicable to prostate and breast or other soft tissue biopsies and for use in conjunction with ultrasonic transducers. Alternative needle configurations are disclosed to improve sample yield, reduce coring and minimize needle fouling.

24 Claims, 14 Drawing Sheets

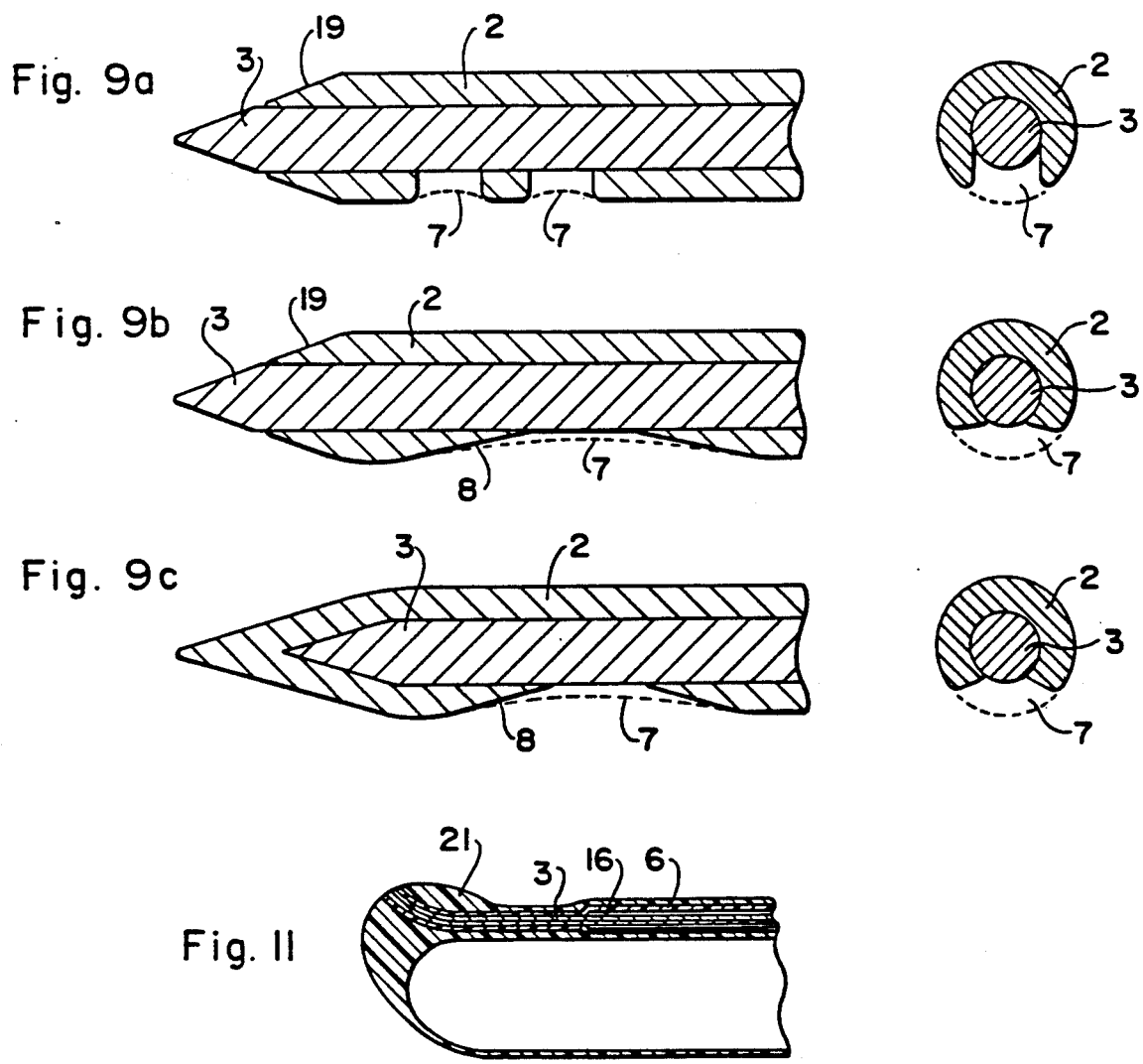

Fig. 12
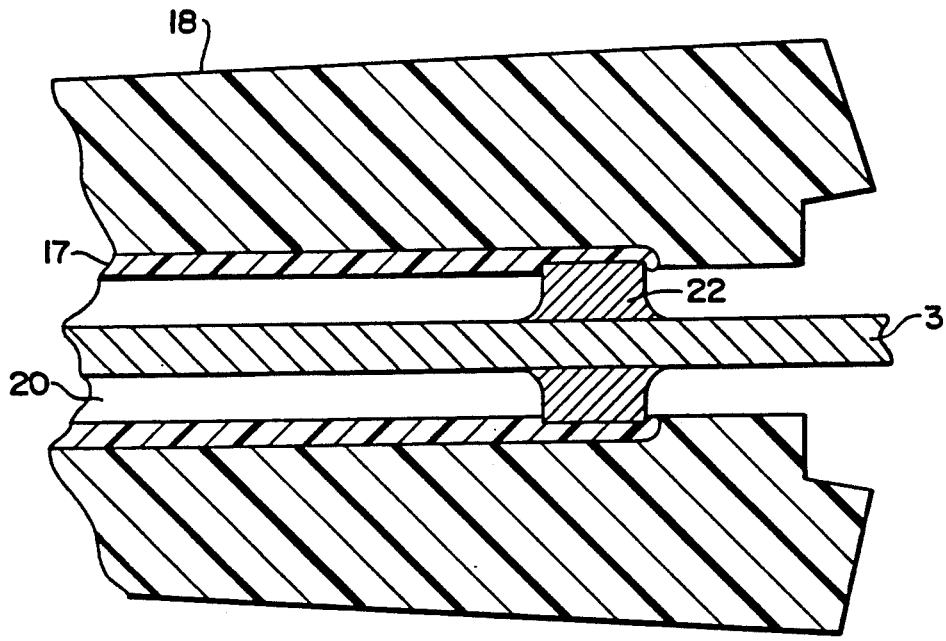
Fig. 10a
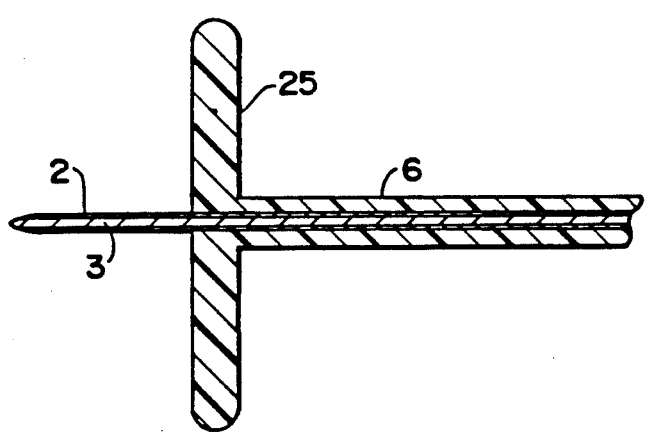
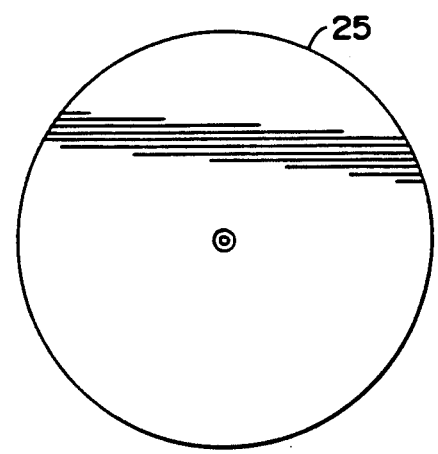
Fig. 10b

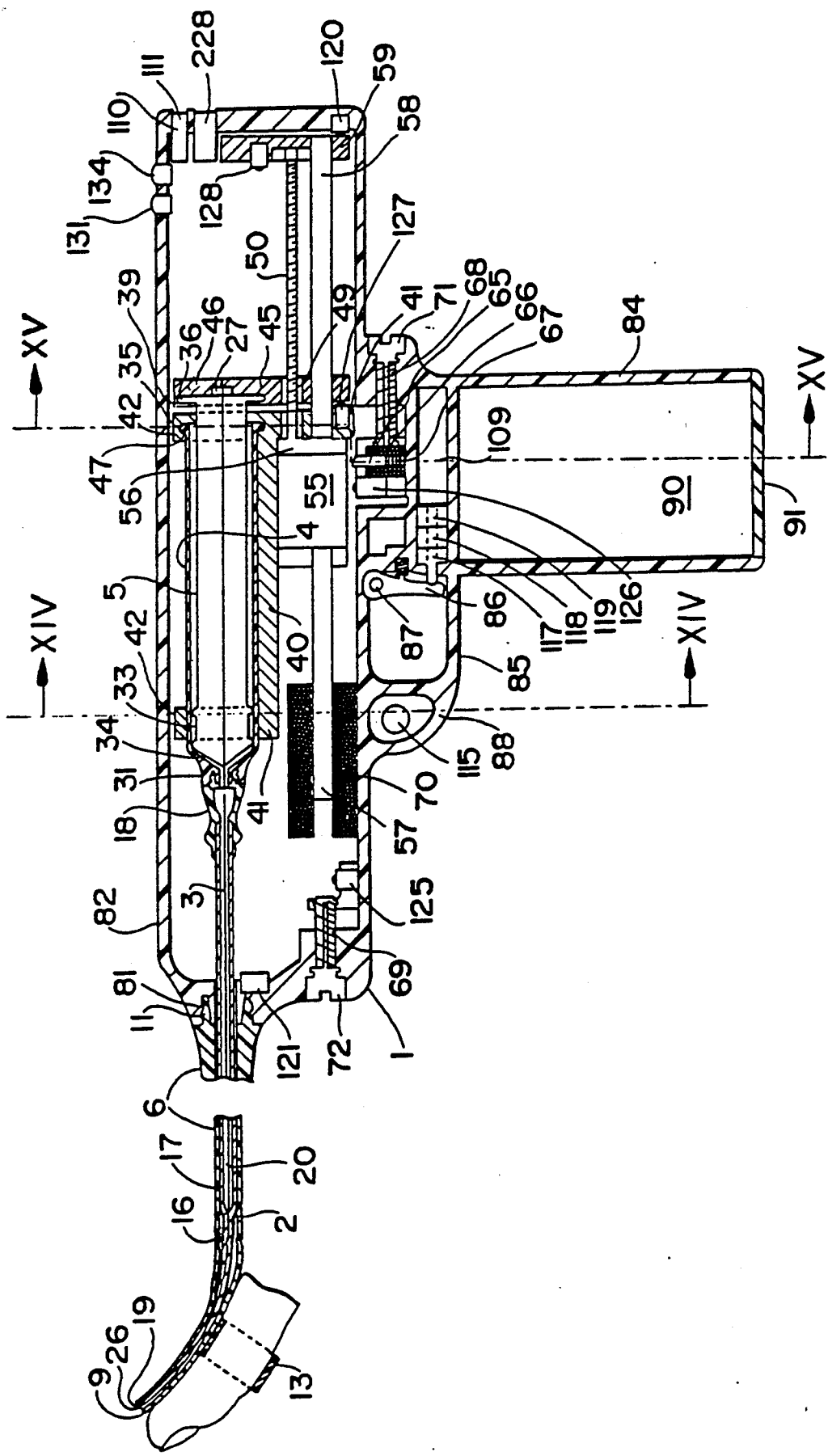

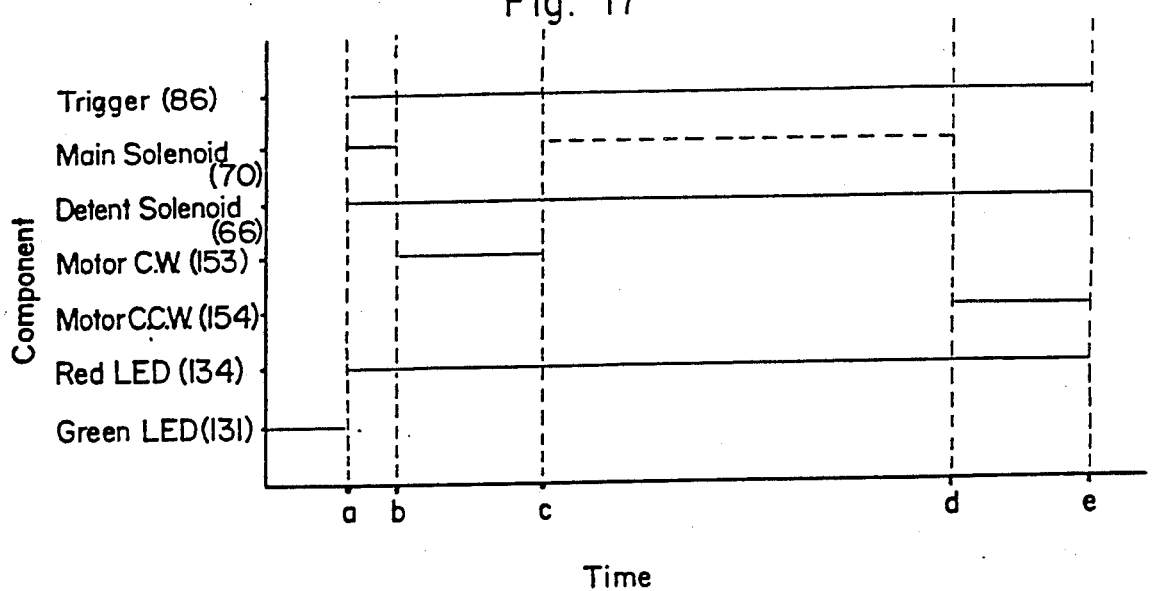
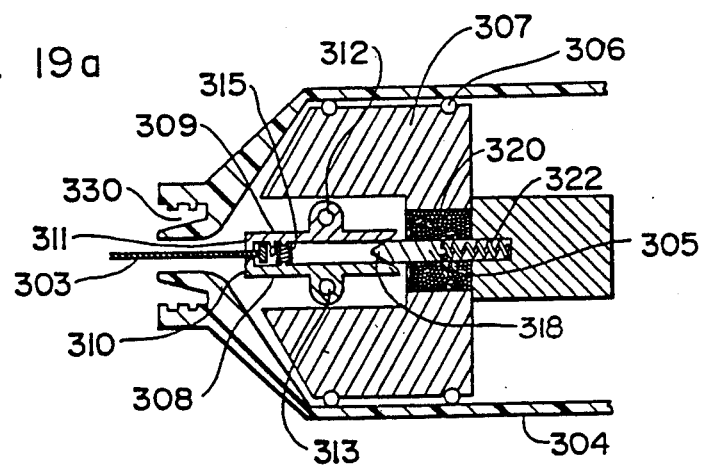
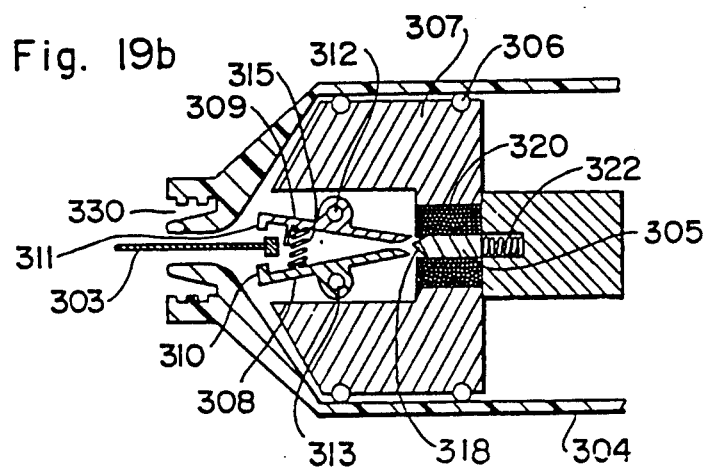

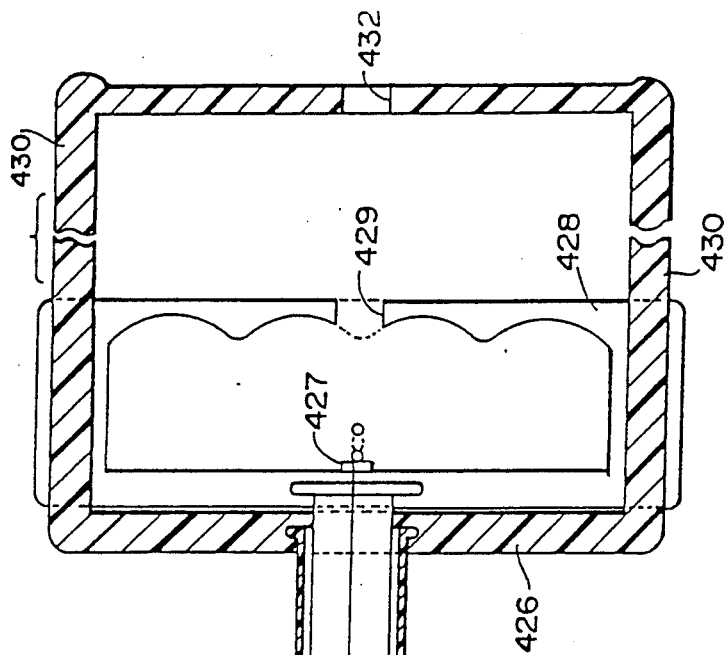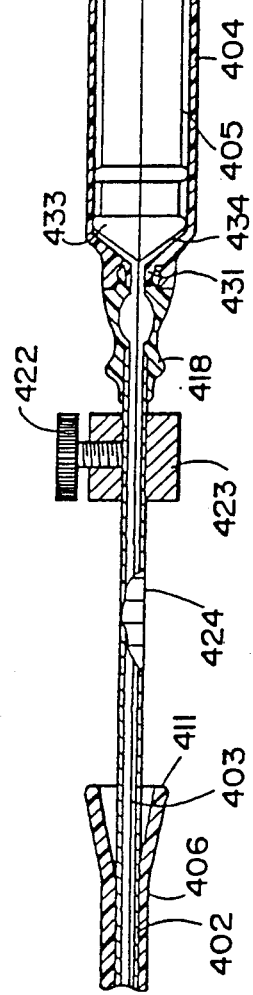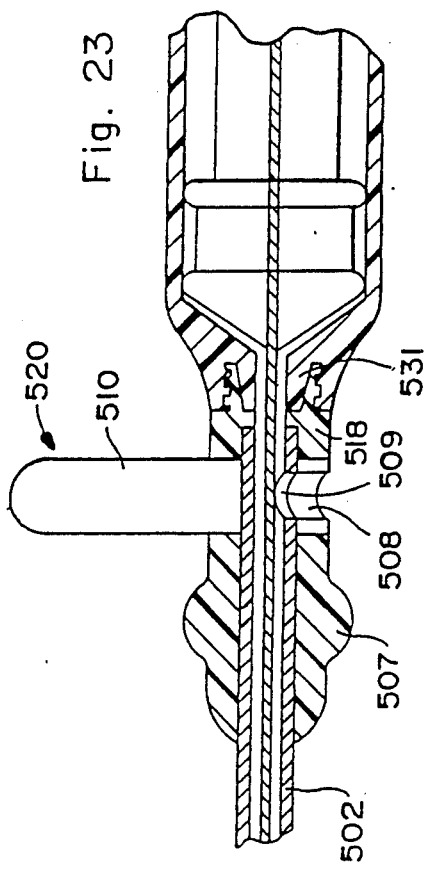

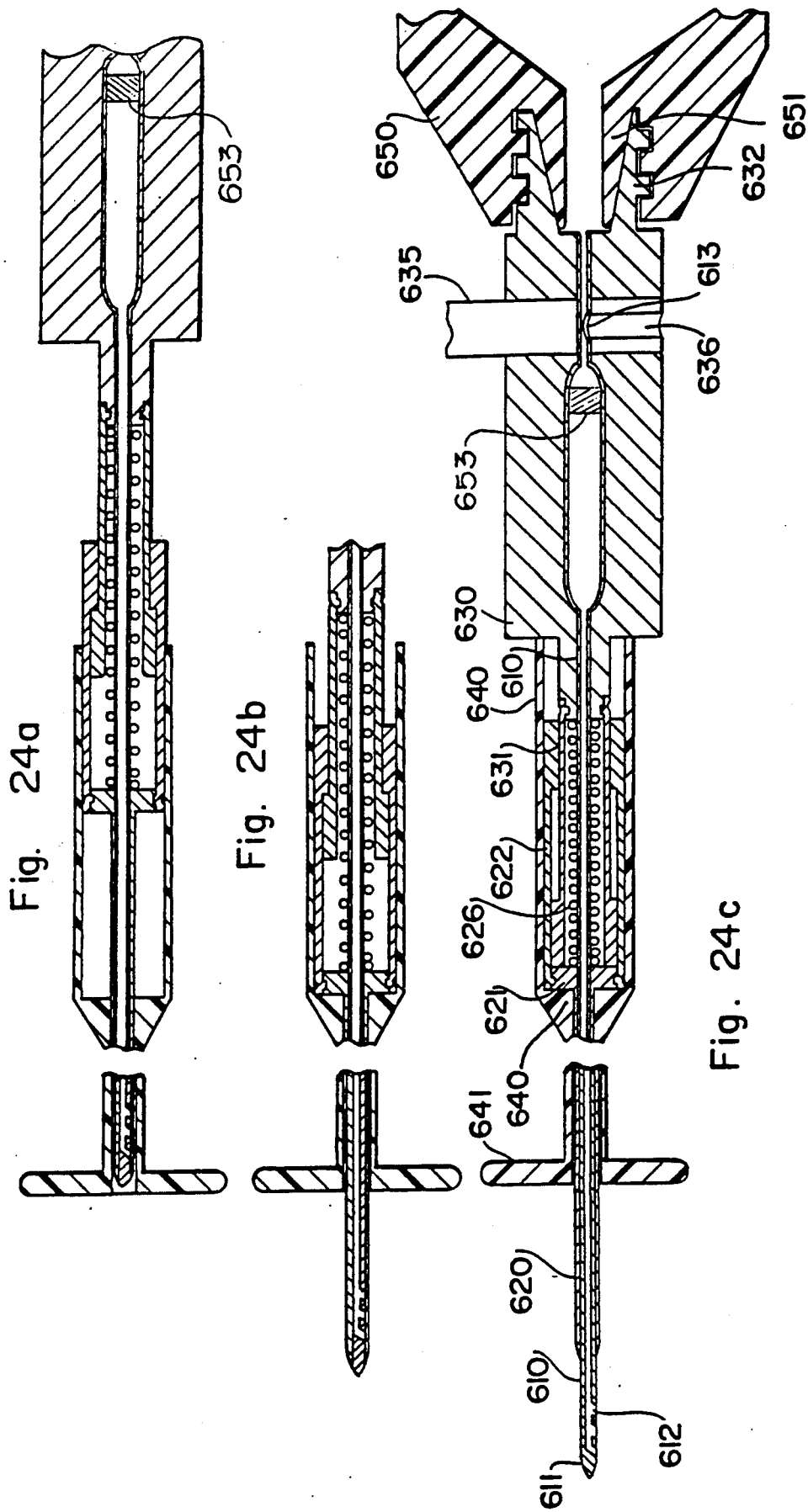

FINE-NEEDLE ASPIRATION CELL SAMPLING APPARATUS

This application is a continuation of application Ser. No. 159,320, filed Feb. 23, 1988, now U.S. Pat. No. 4,989,614, Feb. 5, 1991.

BACKGROUND OF THE INVENTION

The present invention relates to methods and apparatus for taking samples of cells from discrete tissue areas. The taking of such samples is necessary in the cytological diagnosis of suspect tissue areas such as tumors.

Various techniques have been used to take cells from tumors in order to establish whether they are benign or malignant. The choice of a specific technique depends on several factors, including the location and size of the area to be sampled, the susceptibility of the area to complications such as infection, and the ease of use.

One commonly used technique is the so-called core needle biopsy technique wherein a relatively large hollow needle (e.g., 14 gauge) is forced into the tissue to be sampled and then retracted to yield a core sample suitable for histological evaluation. The taking of core needle biopsy specimens is particularly prevalent in the diagnosis of prostatic cancer in the United States. The popularity of this technique is attributed in part to the minimal training required to perform the procedure. In fact, it not infrequently results in complications due to the inevitable traumatization of the tissue by the relatively large needle.

An alternative to the core needle biopsy technique is the so-called fine-needle aspiration technique. Cytological diagnosis with the aid of fine-needle puncture and aspiration started in the late 1950's, when it was shown that individual cells collected from tumors by means of this technique could be recognized and classified. The fine needle aspiration technique offers numerous advantages over core needle biopsy. For example, with respect to the cytological diagnosis of prostatic cancer, fine needle aspiration can be performed as an outpatient procedure without anesthesia or bowel preparation. Further, the patient can be informed of the diagnosis almost immediately and there is an extremely low incidence of complications (1% in 14,000 cases). Moreover, aspiration cytology has proven to be more accurate in prostate cancer diagnosis than conventional core needle histological biopsy. In summary, fine needle aspiration biopsy is an accurate, inexpensive and safe method of diagnosing cancer.

Current fine-needle aspiration apparatus and techniques, however, suffer from several disadvantages, which have contributed to limiting their widespread acceptance in the United States.

U.S. Pat. No. 3,595,217 discloses a method and apparatus for fine needle aspiration biopsy of the prostate. The method and apparatus disclosed in U.S. Pat. No. 3,595,217 are very similar to the method and apparatus commonly used throughout Europe and increasingly used in the United States. However, the disclosed method and apparatus are cumbersome to use, requiring, in practice, at least one highly trained person with an assistant to successfully perform the procedure since the needle is first inserted in the patient, and a syringe is thereafter attached while the operator's hand remains in the patient. Moreover, the disclosed method and apparatus do not readily lend themselves to the use of a stylet during penetration and withdrawal of the needle. Furthermore, the insertion, withdrawal and reciprocation of the needle during the procedure are not precisely determinable since the procedure is performed manually with no means to precisely monitor needle movement. In addition there is a lengthy learning curve that can only be overcome by performing many manual (conventional) fine-needle aspiration biopsies under proper instruction.

U.S. Pat. No. 4,605,011 to Naslund discloses yet another prior art attempt to solve the problems associated with fine-needle aspiration methods and apparatus. The Naslund cell sampling methods and apparatus, however, have several disadvantages. First, because a stylet is not used to occlude the tip of the needle during the aspiration procedure, there is a danger of patient and sample contamination. For example, in prostate aspiration, the absence of a stylet increases the risk of contamination of the aspirated sample and inoculation of the prostate with enteric bacteria present in the rectal vault when the needle is passed through the rectal mucosa into the suspected tumor in the prostrate gland. The Naslund apparatus and method further require that the tip of the biopsy needle be introduced into the suspected tumor without predictability or repeatability, because the operator is unable to precisely determine the forward excursion of the needle when penetrating the target area. Also, the persistence of vacuum in the needle and adjacent connecting tube of Naslund after release of the trigger at the conclusion of the biopsy could tend to cause (i) aspiration of contaminants or debris, such as rectal mucosa and/or bacteria residing in the rectum, and (ii) potential loss of sample into the connecting tube. Furthermore, Naslund employs a single gauge fine needle, thus limiting the total amount and recoverability of cell sample. Accordingly, the Naslund cell sampling apparatus is not well suited for certain applications, such as the cytological diagnosis of prostatic cancer.

Accordingly, it is an object of the present invention to provide an apparatus and method for fine-needle aspiration which simplify and standardize the fine-needle aspiration technique.

It is a further object of the present invention to provide a fine-needle aspiration apparatus and method which allow the needle to be occluded during the penetration and withdrawal stages of the procedure to avoid introducing contaminants into the sample or the region being biopsied.

It is a further object of the present invention to provide a fine-needle apparatus and method which enable a single person to perform the biopsy procedure.

Another object of the present invention is to provide a device capable of performing a fine-needle aspiration biopsy quickly and safely, preferably in an out-patient setting; such as the practitioner's office.

It is a further object of the present invention to provide a fine-needle apparatus and method which will standardize and simplify the aspiration procedure by automatically performing one or more steps of the aspiration procedure.

It is a further object of the present invention to provide a fine-needle aspiration cell sampling apparatus having a failsafe feature which automatically occludes the needle tip, and retracts the needle in emergency circumstances.

It is a further object of the present invention to provide a fine-needle biopsy apparatus which is entirely disposable or in which all parts subject to contamination are disposable.

It is another object of the present invention to provide a fine-needle aspiration apparatus and method which facilitate the collection of cytological samples without coring the tissue in the region being sampled.

It is also an object of the present invention to provide a fine-needle aspiration apparatus and method which facilitate the collection of a sufficient quantity of cells to enable an accurate cytological diagnosis to be made (i.e., malignant vs. benign).

It is a further object of the present invention to provide apparatus and methods which simplify and facilitate the expression of cytological samples retrieved through fine-needle aspiration.

These and other objects will become apparent to those skilled in the art upon reviewing the summary of the invention, and the detailed description and drawings of the preferred embodiments of the invention hereinafter set forth.

SUMMARY OF THE INVENTION

The present invention relates to improvements in apparatus and methods for performing biopsies by fine-needle aspiration of cytological samples. In accordance with the method of the present invention, the operator performing the biopsy locates the sheath in the proximity of the biopsy target area. During this initial location stage, the sheath and needle are positioned with respect to each other such that the needle tip is obscured by the end of the sheath. In accordance with the method, the opening of the needle is occluded during this stage of the fine-needle aspiration procedure. Thereafter, the needle is moved forward with respect to the sheath, causing the occluded needle to enter the target area. Openings in the needle are then unoccluded and vacuum is applied to the needle. The needle is thereafter reciprocated, causing the cytological sample to be drawn into the needle. After a predetermined number of reciprocations (determined by the desired sample yield), the needle openings are again occluded, the vacuum is released and the needle is then withdrawn. Because the needle openings are occluded both during penetration and withdrawal, contaminants are not drawn into the needle. Moreover, occlusion of the needle openings during penetration minimizes the introduction of contaminants from the penetration path to the target area, thereby reducing the chance of infection in the target area.

Disclosed herein are several preferred fine-needle aspiration biopsy apparatus embodiments for performing the above-described method. Each of the preferred embodiments enable the biopsy procedures to be standardized, include mechanisms for occluding the needle during penetration and withdrawal, and renders feasible the performance of the biopsy by a single operator.

A first preferred embodiment of the invention is a fine-needle biopsy apparatus which automatically performs the above-discussed fine-needle aspiration method. In particular, the first embodiment comprises a gun having a syringe and needle. The needle protrudes from the gun and is surrounded by a sheath, which is removably secured to the gun. In operation, the sheath and needle are positioned next to the target area, and the operator initiates the automatic aspiration procedure by sequentially activating safety and trigger mechanisms. After activation, the first preferred embodiment of the present invention automatically initiates the method steps, including (1) penetration of the needle into the target area while the opening of the needle is occluded; (2) unoccluding the needle opening and applying vacuum to the needle; (3) reciprocating the unoccluded needle to collect the cytological sample; (4) again occluding the needle opening and releasing the vacuum; and (5) withdrawing the needle. After the cycle has been automatically completed and the cytological sample has been obtained, the sample is expressed onto a microscope slide by of one of several disclosed methods.

The gun of the first preferred embodiment utilizes a disposable assembly, comprised of a syringe, syringe plunger, variable diameter needle, stylet and sheath. The stylet is connected to the plunger, and is dimensioned such that it occludes the needle opening when the plunger is in its forwardmost position, but unoccludes the needle opening when the plunger is withdrawn. The disposable assembly is removed after operation, and the non-disposable portion of the apparatus (i.e., the gun) is ready for use without sterilization.

The first preferred embodiment is electromechanically operated via solenoids and a D.C. motor. However, D.C. stepping motors or servo motors can be utilized in lieu of one or more of the electromechanical solenoids and D.C. motor to actuate the apparatus. In a modification of the first embodiment, pneumatic cylinders and pistons can be used in lieu of the electromechanical devices for actuating the apparatus.

Numerous safety features are incorporated in the first preferred embodiment of the present invention, including a mechanism for ensuring retraction of the needle into the sheath upon release of the trigger by the operator. An alarm and safety breaker are provided to respectively inform the operator and disable the apparatus should a mechanical or electromechanical problem occur. Furthermore, the automatic apparatus will not operate if there is insufficient power to complete the entire aspiration cycle.

In further modifications of the first preferred embodiment, the syringe and plunger are not disposable, but instead are incorporated within the reusable portion of the apparatus. Only the needle, stylet and sheath are disposable. In this embodiment, the plunger incorporates a grabber mechanism, which is either mechanically or electrically actuated, to grab the stylet for movement with the plunger to, respectively, occlude and unocclude the needle openings.

In a second preferred embodiment of the present invention, the needle, stylet, sheath, and syringe arrangement of the first embodiment of the invention are manually operated in lieu of the automatic apparatus of the first preferred embodiment of the invention. As with the automatic apparatus, the stylet of the manual apparatus occludes the needle opening during the insertion and withdrawl stages of the procedure. A gage and stop are provided to enable the operator to monitor the movement of the needle during the procedure, facilitating standardization of the procedure. As with the automatic embodiment, the procedure can be performed by a single operator without the need for extensive training or experience. The entire apparatus can be disposable or, alternatively, the syringe, plunger, needle, stylet and sheath can be disposable and used with a reusable handle apparatus.

As will be appreciated from the foregoing discussion, the first and second embodiments of the present invention utilize a variable diameter needle and a stylet to selectively occlude the needle opening. Third and fourth preferred embodiments of the invention are also disclosed, in which the stylet is omitted, and the needle is instead occluded during insertion and withdrawal by an outer sleeve, which is retracted during the aspiration procedure to expose the needle openings and allow cytological sample to be drawn into the needle. The third embodiment is manually operated, and the fourth embodiment is automatic.

In each of the above-discussed embodiments, several alternative sheath designs can be implemented depending upon the type of biopsy to be performed. For transrectal biopsies of the prostate, a sheath having a finger guide and handle portion is used to facilitate manipulation by the operator. For biopsies of soft, fleshy tissue regions (e.g., the breast) a disc-like sheath end can be implemented to stabilize and locate the sheath and needle on the fleshy tissue. The sheath can also be designed to accommodate an ultrasonic transducer so that the target area can be ultrasonically probed to position the sheath and needle. Additionally, several alternative needle designs can be implemented to reduce coring by the needle and minimize needle fouling.

BRIEF DESCRIPTION OF THE DRAWINGS

The invention will now be described with reference to the drawings wherein like reference numerals refer to similar parts throughout the several views and in which:

FIGS. 9a-9c are cross-sectional views of alternative needle and stylet arrangements;

FIGS. 10a and 10b are cross-sectional views of an alternative needle and sheath arrangement of the present invention;

FIG. 11 is a cross-sectional view of a further alternative needle and sheath arrangement of the present invention;

FIG. 12 is a cross-sectional view of a modification of the needle and sheath assembly of the present invention;

FIG. 13 is a cross-sectional elevation of a first preferred embodiment of fine-needle aspiration apparatus of the present invention;

FIG. 17 is a schematic diagram illustrating the control sequence of the first embodiment of the present invention;

FIGS. 19a and 19b are cross-sectional views illustrating modifications of the first embodiment of the present invention;

FIG. 22 is a cross-sectional view of a manual second embodiment of the present invention;

FIG. 23 is a cross-sectional view of a modification of the manual second embodiment of the present invention;

FIGS. 24a-24c are cross-sectional views of a manual third embodiment of the present invention.

DETAILED DESCRIPTION OF THE INVENTION

Figure 1A:
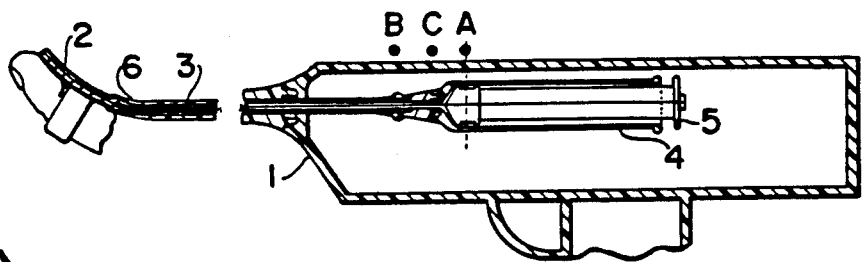
FIGS. 1a-1f are schematic cross-sectional views illustrating the method of the present invention.

FIGS. 1a-1f schematically illustrate the positions of a needle 2, stylet 3, syringe 4 and plunger 5 relative to a fixed casing 1 and sheath 6 during a fine needle aspiration procedure using the first preferred embodiment of the apparatus of the present invention. More specifically, the schematic representation illustrates the movements of a first movable unit comprised of needle 2, syringe 4 and the means for longitudinally moving the same, and a second movable unit comprised of stylet 3, plunger 5 and means for longitudinally moving the same. The first and second movable units are adapted for movement relative to one another or together as a carriage assembly. Many of the movements of the needle, stylet, syringe and plunger illustrated in FIGS. 1a-1f are common to several embodiments of the invention, as discussed in more detail herein with reference to specific embodiments of the invention.

In FIG. 1a, the carriage (including the first and second movable units) is in its initial position "A". To commence aspiration of suspect tissue, the operator manually aligns the tips of the sheath, needle and stylet at or near the region to be sampled, hereinafter referred to as the target area. The operator then initiates the automatic aspiration procedure by, for example, manually triggering a switch located adjacent a pistol grip of the apparatus.

Figure 1B:
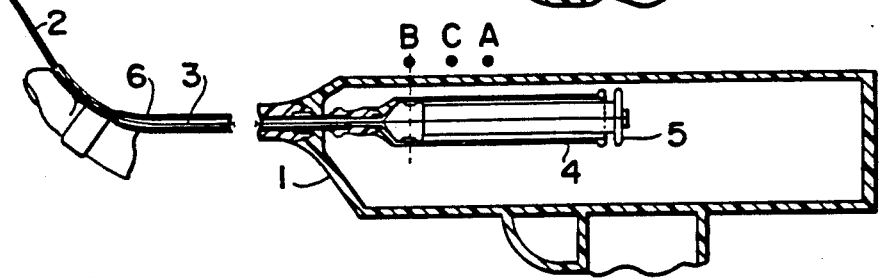

In accordance with a first preferred embodiment of the present invention, upon initiation of the automatic aspiration procedure, the carriage (and hence the needle 2 and stylet 3) moves forward a first predetermined distance to the position "B" shown in FIG. 1b. This movement advances the tips of the needle and stylet past the end of the sheath into the target area. This step is particularly desirable for those instances where it is not practical to manually position the tips of the needle and stylet at the target position (e.g., when the target area is in a remote region, such as the prostate gland). Automation of this step facilitates standardization of the aspiration procedure and helps ensure that the operator does not overshoot or undershoot the target area. When the present invention is used in an environment where the tips of the needle and stylet can be accurately, conveniently and safely manually positioned into the target area, this step can be omitted.

Figure 1C:
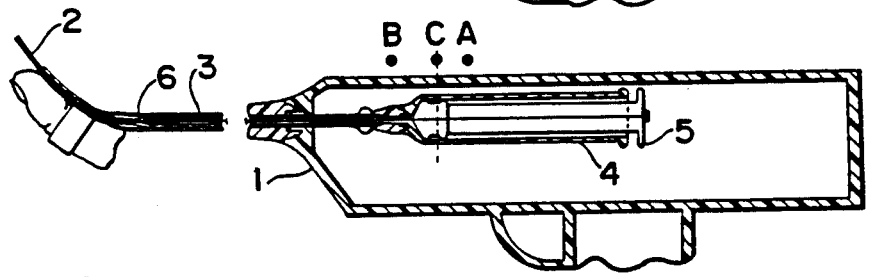

FIG. 1c illustrates the next step in the operation of the first embodiment, wherein after the initial forward movement of the carriage (position "B"), the carriage moves backwards a second predetermined distance to a position "C" located between positions "A" and "B". This step, which is omitted in manual embodiments of the invention, is in accord with a fail-safe aspect of the present invention, discussed in more detail below, whereby when power is cut off from the device, all carriage components are brought to a fully retracted position.

Figure 1D:
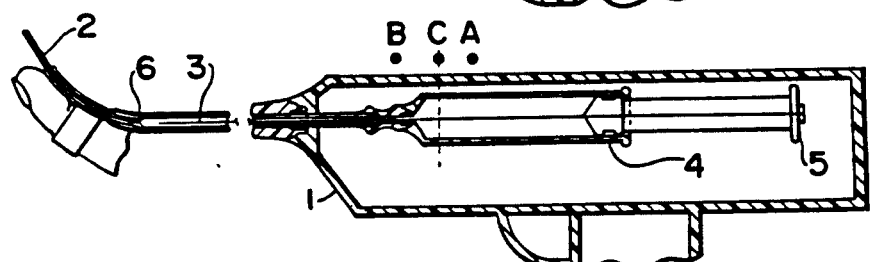

FIG. 1d illustrates the next step of the aspiration procedure in which the second movable unit, which includes the plunger 5 and the stylet 3, is retracted relative to the first movable unit, which includes the syringe 4 and the needle 2, to an extended carriage position. In accordance with the present invention, and as discussed in more detail herein, this step serves at least two important functions. First, retraction of the stylet provides a passage between the tip of the needle and a larger diameter cell sample storage portion of the needle located rearwardly of the tip of the needle. Second, retraction of the plunger simultaneously reduces the pressure in the cell sample storage portion of the needle. Because the retraction of the second movable unit relative to the first movable unit both opens a passage between the tip of the needle and the cell sample storage portion of the needle and creates a partial vacuum in the cell sample storage portion of the needle, a suction force is created at the tip of the needle causing sample material to be drawn into the cell sample storage portion of the needle.

Although cell sample is immediately drawn into the cell sample storage portion as the plunger is withdrawn, reciprocation of the needle within the target area is required to increase the sample yield. Thus, in accordance with the present invention, the carriage (while in the extended position) is reciprocated between the positions illustrated in FIGS. 1d and 1e, i.e., between positions "B" and "C".

After sufficient sample has been collected, the reciprocation cycle terminates. The second movable unit (including the stylet 3 and plunger 5) is then returned to a forward position as indicated in FIG. 1f so as to occlude the passage between the needle tip and the cell sample storage portion of the needle. Additionally, the return of the stylet and plunger to the forward position seals and removes the vacuum from the cell sample storage portion of the needle.

After the second movable unit is fully returned to the position shown in FIG. 1f, the carriage is returned to the position shown in FIG. 1a thus completing the aspiration procedure. The operator then withdraws the apparatus from the patient, removes the sheath, opens a cover of the apparatus, removes the syringe and needle from the apparatus, disconnects the syringe and stylet from the needle, connects a second syringe (filled with air) to the needle, and expresses the collected cell sample from the needle onto a slide. At this time, the cytological analysis of the cell sample can be performed. Additionally, since the apparatus is restored to its original state as shown in FIG. 1a and all components that were in contact with the patient (i.e., needle 2, stylet 3, sheath 6) are discarded, the apparatus is ready to receive a new sterile sheath, needle and syringe assembly for the next fine needle aspiration procedure. Sterilization of the reusable portion of the apparatus is not required.

An important feature of the present invention is the unique construction of the needle and stylet which allows the aspiration procedure to be completed automatically. Moreover, the configuration of the needle and stylet obviates the need for removal of the stylet before commencing the procedure and allows the sample storage portion of the needle to be fully sealed during both the penetration and withdrawal stages of the procedure. Finally, the configuration of the needle and stylet facilitates removal of a cytological sample without coring the target area.

Figure 2:
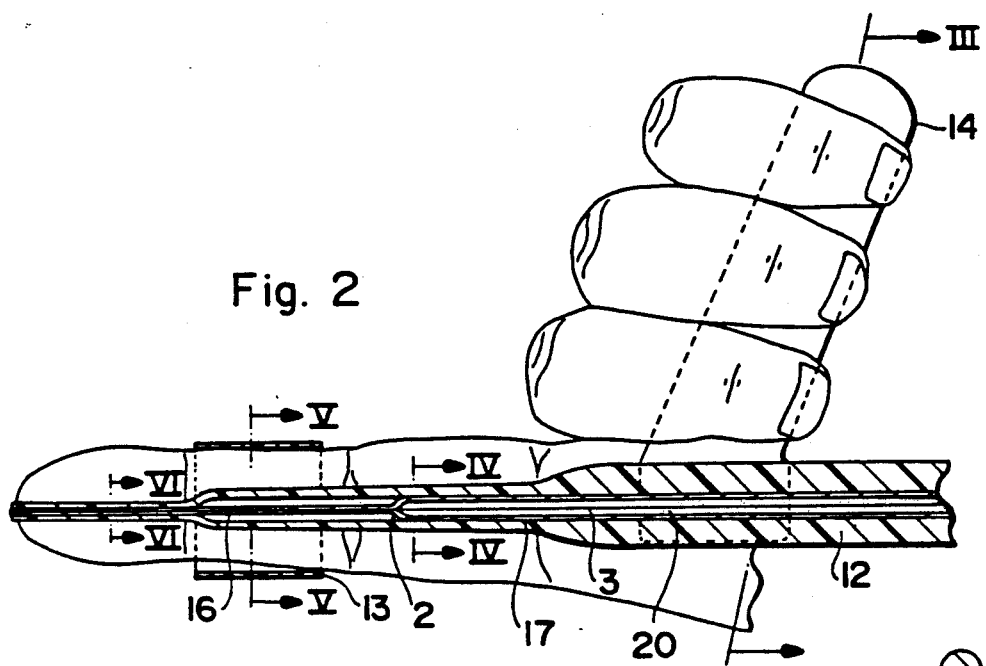
FIG. 2 is a cross-sectional view of a needle and sheath assembly of the present invention.
Figure 3:
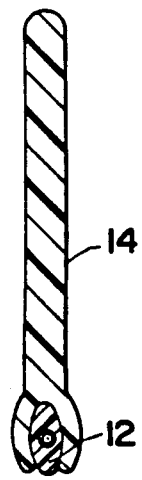
FIG. 3 is a cross-sectional view of the needle and sheath assembly of FIG. 2 taken along line III—III
Figure 4:
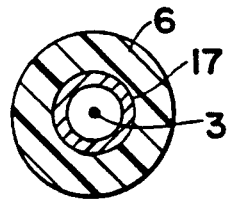
FIG. 4 is a cross-sectional view of the needle and sheath assembly of FIG. 2 taken along line IV—IV.

A preferred needle construction is described hereinafter with reference to FIGS. 2-8. FIG. 2 is a partial cross-sectional view of a needle 2, a stylet 3 and a needle sheath 6. As shown in FIGS. 2-8, the stylet 3 has a uniform circular cross-section along its length. The needle tube, however, has a variable cross-section. In particular, the needle includes a narrow diameter portion 16 (e.g., 22 gauge) and an expanded diameter portion 17 (e.g., 18 gauge). Both portions of the needle 2 are hollow thus permitting the stylet 3 to extend therethrough.

Figure 8:
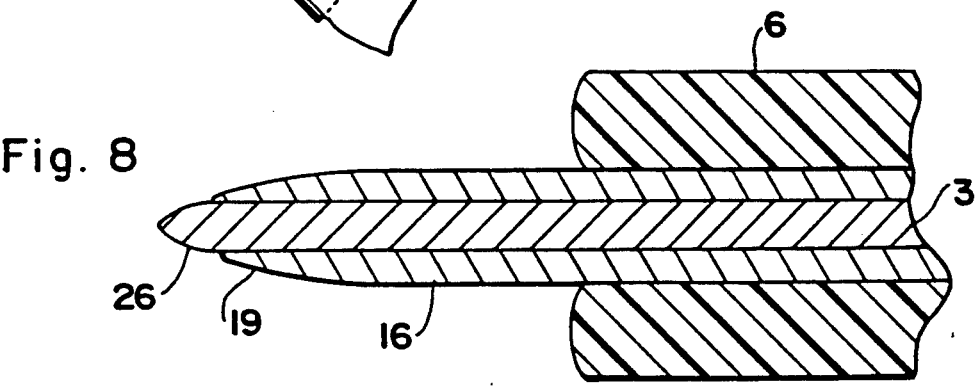
FIG. 8 is an enlarged cross-sectional view of the sheath and needle tip of the needle and sheath assembly of FIG. 2.

The exterior diameter of the stylet is substantially the same as the interior diameter of the narrow portion 16 of the needle so that when the stylet extends fully through the narrow diameter portion 16 of the needle, the stylet occludes the tip 19 of the needle and substantially occupies the entire interior space of the narrow portion of the needle to thereby seal the needle. Further, when in the fully extended position, the tip of the stylet 26 and the tip of the needle 19 are substantially continuous so as to provide a substantially continuously tapering leading edge for effectively penetrating and separating tissue without coring when the needle and stylet protrude beyond the sheath as illustrated in FIG. 8.

The interior surface of the expanded portion 17 of the needle has a larger diameter than stylet 3. Thus, even with the stylet extended into the expanded portion of the needle, a space is provided between the exterior diameter of the stylet and the interior diameter of the expanded portion of the needle. This space defines a chamber or volume, which is referred to herein as the cell sample storage portion 20 of the needle. Cellular material drawn into the needle is collected in the cell sample storage portion for storage until the needle is removed from the target area and the sample is thereafter expressed in the manner described above.

The needle sheath 6 shown in FIGS. 2-8 functions to safely guide the needle to the target area, and prevents patient or operator injury. Significantly, and as discussed in more detail below, when the device is in its initial position, the tip of the needle does not extend beyond the sheath. This prevents inadvertent puncture and resulting infection of the operator or patient which might result from puncture by a protruding needle, and enables safe guidance of the sheath to the proximity of the target area.

Figure 5:
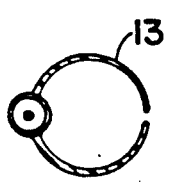
FIG. 5 is a cross-sectional view of the needle and sheath assembly of FIG. 2 taken along line V—V.
Figure 6:
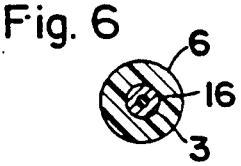
FIG. 6 is a cross-sectional view of the needle and sheath assembly of FIG. 2 taken along line VI—VI.
Figure 7:
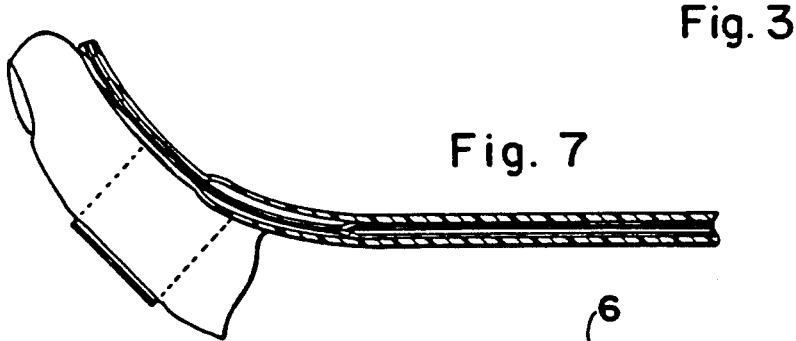
FIG. 7 is partial side cross-sectional view of the needle and sheath assembly of FIG. 2.

As illustrated in FIGS. 2, 5 and 7, in some applications (e.g., when performing a trans-rectal prostate biopsy), a finger guide 13 is provided at or near the end of the needle sheath 6 to assist the operator in manipulating the tip of the sheath. Additionally, to facilitate manipulation of the needle assembly, a sheath positioning handle 14 is provided. Handle 14 is attachable (e.g., by snap fit) to the sheath 6 at any desired location along a handle attachment area 12 so as to be positionable for either right or left hand usage and longitudinally adjustable.

FIGS. 9a-9c illustrate modified needle embodiments which may be implemented to increase the yield of sample collected during the fine needle aspiration procedure and/or to minimize coring which occurs during the procedure. In particular, radially extending ports or holes 7 are provided proximate the tip for cell collection during the aspiration procedure. In the embodiments of FIGS. 9a and 9b the ports are provided in addition to the opening at needle tip 19. In the embodiment of FIG. 9c, the opening at needle tip 19 is omitted, and only side ports are utilized for sample collection. As illustrated in FIG. 9a, a series of holes 7 can be provided at longitudinally spaced locations. Additionally, in a further embodiment (not shown) holes or ports can be radially spaced about the circumference of the needle to facilitate sample collection. If several ports are spaced in the radial direction about the circumference, it will be appreciated that such ports should be located only on one circumferential segment of the needle of less than or equal to 180° to facilitate subsequent expression of the sample onto a microscope slide. As illustrated in FIGS. 9b and 9c, the ports can have a gradual chamfer 8 to reduce coring of the tissue being sampled and to minimize fouling of the holes or ports with tissue and debris. Additionally, the closed tip design of FIG. 9c facilitates tissue separation and reduces coring during reciprocation of the needle.

A modified sheath is illustrated in FIGS. 10a and 10b. Although the sheath and finger guide illustrated in FIGS. 2-8 are suitable for use in certain applications, including trans-rectal prostate biopsies, it is not ideally suited for biopsy applications in fleshy tissue or where the target area is proximate to the surface of the skin. The embodiment ilustrated in FIGS. 10a and 10b is identical to the embodiment of FIGS. 2-8, except that finger guide 13 is omitted and sheath 6 defines a disc-shaped sheath tip 25 at its distal end. The disc-shaped sheath tip is adapted to be pressed firmly against the skin in the proximity of the target area, and functions to stabilize the sheath while the biopsy is being performed. As will be appreciated by those ordinarily skilled in the art, numerous sheath configurations could be implemented to adapt the present invention to biopsies in various regions of the body.

A further modification of the sheath is illustrated in FIG. 11, which renders the apparatus suitable for use with a conventional ultrasonic probe. Sheath 6 is secured within a probe retainer 21, which is shaped to conform to and accommodate a conventional ultrasonic probe (not shown). In prostate biopsy applications, for example, the probe within its retainer is inserted trans-rectally in lieu of the operator's finger to locate the target area. Upon location of the target area, the sheath is positioned such that the target area will be penetrated by the needle upon actuation of the apparatus. The aspiration procedure is then performed in the manner herein described.

FIG. 12 illustrates a further modification of the needle and stylet assembly. As illustrated in FIG. 12, a filter 22 is mounted within the wider diameter portion 17 of needle 2 at a connection end 18 thereof. Filter 22 is annular in shape, and defines a center region through which stylet 3 is tightly inserted. Filter 22 ensures that the sample withdrawn from the target area remains within the cell sample storage portion 20 of the needle, and is not drawn into the syringe body upstream of the filter. The filter further functions to wipe the stylet as the stylet moves within the needle. By wiping the stylet and capturing the sample within the cell sample storage portion 20 of the needle, subsequent expression of the sample onto the microscope slide is facilitated and the amount of sample which remains unexpressed from the needle is reduced. Furthermore, the filter functions to wipe the stylet clean when the plunger and stylet are removed for expression purposes, thereby reducing the dangers of operator infection.

FIGS. 13-16 illustrate, in detail, the structure of a first preferred embodiment of the fine-needle aspiration cell sampling apparatus of the present invention. The apparatus includes a casing 1, needle 2, sheath 6, stylet 3 syringe 4 and plunger 5, as discussed above. The needle can be of any of the constructions and include one or more of the features described above. The sheath can also be of any of the configurations described above and should be selected in view of the particular application for which the apparatus is being used. The needle is connected to syringe 4 via conventional luer-lock connections 18, 31. Similar connections 11, 81 join sheath 6 to casing 1. The syringe 4 may be of conventional construction or of a construction especially suited for use in conjunction with the first embodiment of the fine needle aspiration cell sampling apparatus. Stylet 3 is fixed to plunger 5 and is removable therefrom via stylet grip 27. The plunger and the syringe together define a variable volume air chamber 34 through which the stylet extends. As is well known in the art, the plunger 5 is provided with a plunger head 33 which includes at least one sealing portion to maintain an airtight fit between the perimeter of the plunger head 33 and the interior of the syringe 4.

Figure 14:
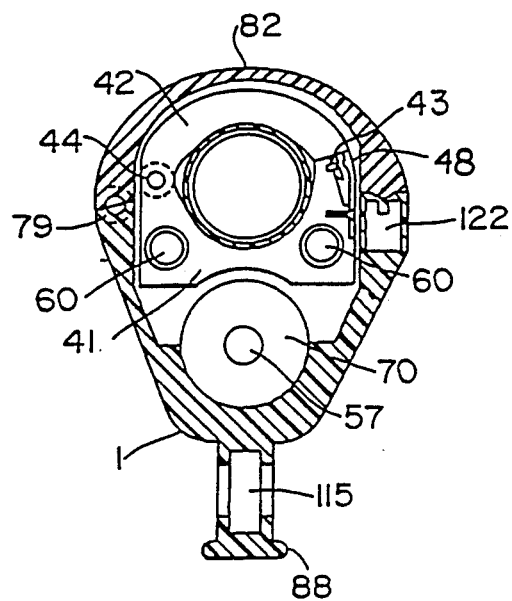
FIG. 14 is a cross-sectional view of the fine-needle aspiration apparatus of FIG. 13 taken along line XIV—XIV.
Figure 15:
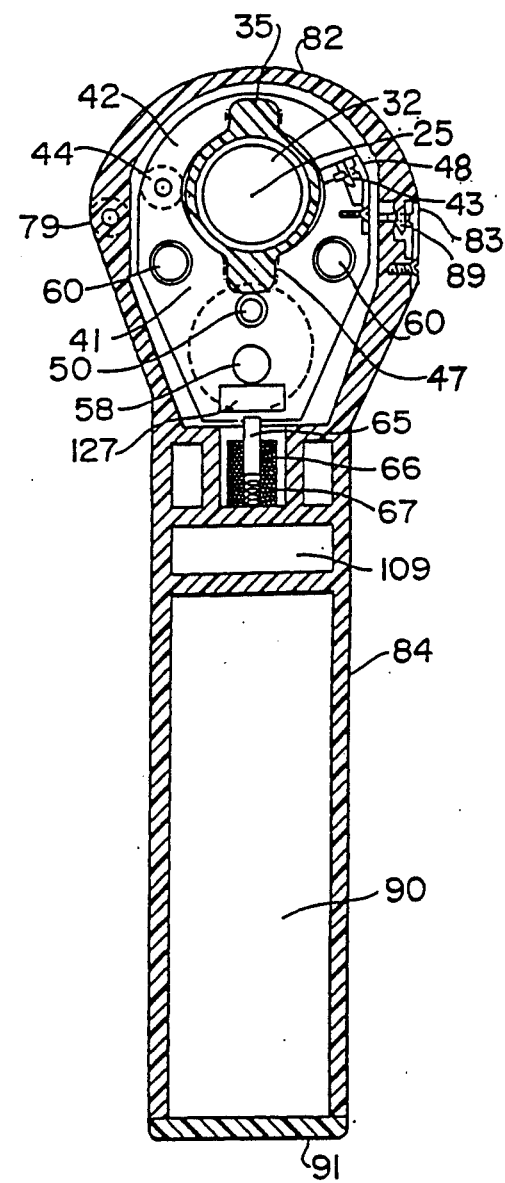
FIG. 15 is a cross-sectional view of the fine-needle apparatus of FIG. 13 taken along line XV—XV.
Figure 16:
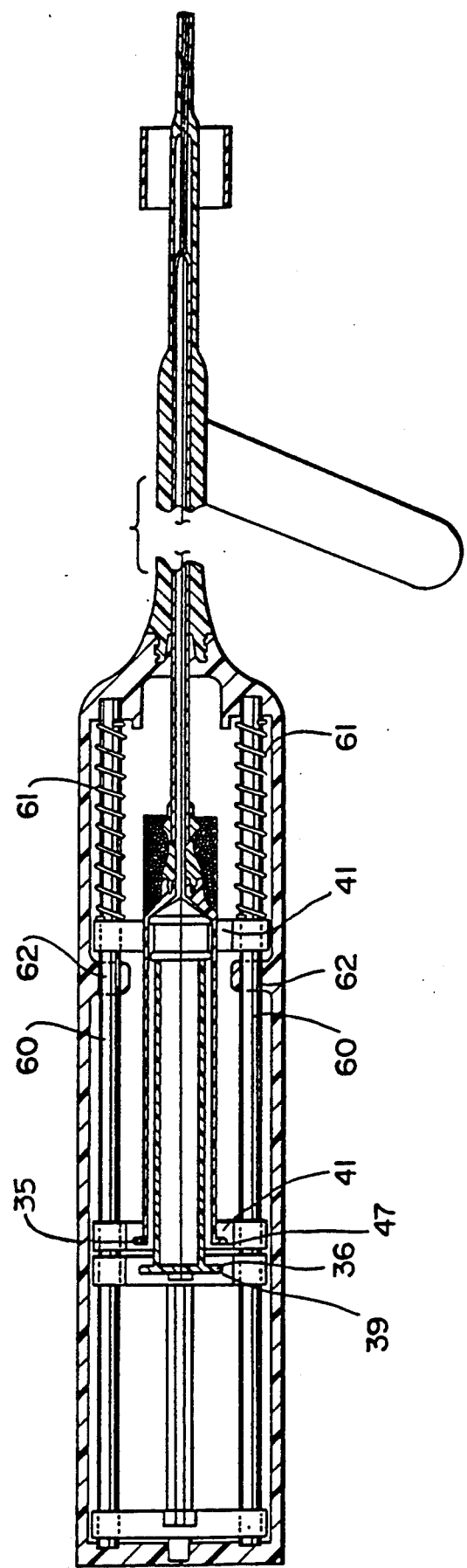
FIG. 16 is a top cross-sectional view of the fine-needle apparatus of FIG. 13.

As illustrated in FIGS. 14-16, a pair of syringe carriage guide rods 60 are supported by and fixed with respect to the casing 1 at syringe guide rod supports 62 so as to extend parallel to the needle 2 and syringe 4. A pair of U-shaped syringe support brackets 41 and U-shaped plunger bracket 45 are slidably supported on the guide rods 60. As shown in FIG. 13, the syringe support brackets 41 are connected to one another by a syringe carriage 40. The rear U-shaped syringe support bracket 41 includes locking groove 47 for receiving a syringe body flange 35. Plunger support bracket 45 similarly has locking groove 39 for receiving plunger body flange 36. Thus, U-shaped brackets 41 support the syringe 4 (and the needle 2 connected thereto) for movement in the longitudinal direction of the guide rods 60. Similarly, plunger head 33 and U-shaped plunger support bracket 45 support the plunger for movement in the longitudinal direction of the guide rods 60. A pair of helical springs 61 are provided coaxially with portions of the guide rods 60, respectively. The springs 61 extend between a front end of the casing 1 and a side portion of forward U-shaped support bracket 41 and function to bias the U-shaped bracket in a rearward direction.

As shown in FIGS. 13-15, front and rear syringe retainers 42 are pivotally secured to the front and rear U-shaped syringe support brackets 41 by hinges 44. Latches 43 lock the syringe retainers 42 to the U-shaped brackets 41 to secure the syringe within the U-shaped brackets. Latches 43 are unlatched by syringe retainer release buttons 48 (FIGS. 14 and 15). A similar hinge latch and release button (not shown) are employed to secure a plunger retainer 46 to the U-shaped plunger support bracket 45.

Additionally, as shown in FIGS. 14 and 15, a top portion or cover 82 of casing 1 is pivotable with respect to the remainder of the casing about a hinge 79. A latch assembly, comprised of latch 89 and release button 83, is provided to enable selective locking of the cover portion 82 of the casing to the remainder of the casing. Cover 82 is spring biased to the open position by a conventional spring (not shown). In use, latch assembly 83, 89 is released and the pivotable cover portion 82 of the device is swung open when it is necessary to replace the disposable syringe assembly, comprised of the needle 2, stylet 3, syringe 4 and plunger 5. A cover switch 122 (FIG. 14) is provided to sense closure of the cover and to prevent operation of the apparatus when the cover or top portion 82 is open, as described in more detail below. Alternatively, or in addition, a sheath switch 121 is provided at the sheath connection to prevent operation of the apparatus when the sheath has not been connected in the manner described below.

A pair of signal LED's 131, 134 are provided on a top portion of the casing. More specifically, a red LED 134 is provided to indicate that an aspiration procedure is in progress and a green LED 131 is provided to indicate that the device is ready for operation. Flashing of either of the LED's indicates an operational fault as discussed in detail below.

The apparatus further includes a main solenoid 70 which, when energized, drives a syringe carriage drive bar 57 against the operative bias of springs 61. The syringe carriage drive bar is secured to an assembly, including a plunger motor 55, plunger motor gear box 56, lead screw support bar 58 and lead screw support bar end plate 59. The motor 55 and reduction gear box 56 are conventional and need not be discussed further herein.

The output of gearbox 56 rotatably drives a plunger lead screw 50 which in turn linearly drives plunger support bracket 45 via a threaded nut portion 49 of support bracket 45. The rearward end of lead screw 50 is rotatably journaled in end plate 59 in suitable bearings or bearing surfaces.

As is apparent from the foregoing, the syringe 4, needle 2, syringe support brackets 41, syringe carriage 40, motor 55, gearbox 56, drive bar 57, lead screw 50, lead screw support bar 58 and end plate 59 are movable longitudinally together as a first movable unit. Additionally, stylet 3, plunger 5 and plunger support bracket 45 are movable longitudinally together as a second movable unit. Moreover, when the lead screw 50 is not rotated, the first movable unit and second movable unit are fixed with respect to one another and movable longitudinally together as a carriage assembly. The first movable unit, second movable unit, and carriage assembly are all constrained to move longitudinally only along guide rods 60.

A spring loaded detent 65 is provided to prevent retraction of the drive bar 57 and the remainder of the carriage assembly beyond a predetermined point corresponding to the position "C" in FIG. 1. Detent 65 is spring biased into a retracted position to allow retraction of the carriage assembly beyond point "C" when the power is off, as described in detail below. A detent solenoid 66 is provided to force detent 65 upwards against the bias of spring 67, when actuated, thereby preventing the retraction of the carriage assembly beyond point "C".

The rearward retraction limit defined by detent 65 (i.e., corresponding to position "C" in FIG. 1) is adjustable via detent positioning screw 68 threaded to casing 1. The positioning screw is adjustable at detent positioning dial 71 such that the precise point of position "C" is settable by the operator with a screwdriver or special tool adapted to accommodate the detent dial face. The forward excursion of the carriage assembly (corresponding to position "B" in FIG. 1) is limited by adjustable drive bar stop screw 69. Stop screw 69 is threaded to the casing 1 and is adjustable via drive bar stop dial 72 to vary the location of position "B". The total operational excursion of the carriage assembly is thus adjustable via detent positioning dial 71 and drive bar stop dial 72.

A lower portion of casing 1 defines a pistol grip 84 having a chamber 90 for storing a battery 92 (not shown in FIG. 13). Battery 92 is removable and is accessed via a cover 91. A particularly suitable power source is a conventional rechargeable Ni-Cad battery. Of course, other conventional power sources can be used. A battery low voltage sensor 113 (not shown in FIG. 13) is provided within chamber 90. Trigger 86 pivots on trigger pivot 87 and is located within trigger guard 85. The trigger is operatively connected to operational control switch 117, main solenoid cut-off switch 118 and detent solenoid cut-off switch 119, discussed in more detail below. Located forward of trigger 86 on safety guard 88 is safety switch 115. Safety switch 115 and trigger 86 may be operated by either the right or left hand. As described in detail below in connection with the control circuitry, the safety switch 115 must be activated before activating the trigger switch 86 to enable the device.

Several other switches and sensors are included to control and monitor the operation of the apparatus. Power switch 110 is provided to energize the electrical and electromechanical components of the apparatus. A power switch breaker 111 deenergizes the apparatus upon completion of an operational cycle. Front drive bar sensor 125 and rear drive bar sensor 126 are respectively fixed to the adjustable drive bar stop screw 69 and the detent assembly 65, 66 and respectively sense the forwardmost and rearwardmost excursion of the carriage. A plunger front limit sensor 127 is fixed to syringe support bracket 41 and senses when plunger support bracket 45 is in its forwardmost position. Plunger rear limit sensor 128 is fixed to lead screw support bar end plate 59 and senses when the plunger support bracket 45 is in its rearwardmost position. Origin sensor 120 is fixed to the rear of casing 1 and senses when the carriage assembly has returned to the origin position (i.e., corresponding to position "A" in FIG. 1). Switches or sensors 125, 126, 127, 128 and 120 may be conventional microswitches, Hall-effect switches or any other well known or suitable switches sensors, including, but not limited to, inductive, optical, fluidic, mechanical or electromechanical switches or sensors.

Furthermore, although the carriage and the detent 65 are described as controlled by main solenoid 70 and detent solenoid 66, either or both solenoids could be substituted with other appropriate means, including, but not limited to, D.C. servo or stepping motors with appropriate linkages providing the desired reciprocatory movements.

Having thus described the structure of the first preferred embodiment of the present invention, the following is a discussion of the mechanical operation of the first embodiment of the fine-needle aspiration apparatus and method of the present invention. For purposes of this discussion, it is assumed that cytological biopsy of a suspicious area of the prostate gland is to be performed.

Before a biopsy is initiated, the suspected tumor area must be examined and assessed as to its dimensions and distance from the proposed entrance point of the needle tip 19. In operation, the needle excursion is determined by the positions of the detent positioning screw 68 and the drive bar stop screw 69. To accommodate dimensional variations in the size and location of target areas, changes of the screw settings can be made manually by using the dial adjustment tool to turn the multi-turned-numerically-indicated dials 71 and 72. First the distance of the suspected tumor area from the entrance point of the needle tip 19 is set on the detent positioning screw 68 via dial 71. Thereafter, the desired total distance the needle tip 19 should traverse during the reciprocation mode is set on the drive bar forward stop screw 69 via dial 72. Dial 72 should thus be adjusted to a setting equalling the initial depth of the target area (i.e., the setting of dial 71) plus the diameter of the target area in millimeters. For example, if the depth of the forward boundary of the target area is assessed to be 5 mm and its diameter 15 mm, then dial 71 is set at 5 mm and dial 72 at 20 mm.

The operator thereafter ensures that a charged battery 92 is installed in the apparatus by closing the casing cover 82 and turning on the power switch 110 to check the charge level of the battery. Green LED 131 will flash if insufficient charge remains to safely complete the cycle, as described in more detail below in connection with the control circuit.

The operator thereafter selects an appropriate sterile dispensable syringe and sheath assembly for the procedure being performed. Casing cover 82 is thereafter opened by depressing the cover release button 83 until the casing cover pops open. Syringe retainers 42 and the plunger retainer 46 are similarly opened by depressing their respective release buttons until they pop open. The operator then grasps the disposable syringe and sheath assembly, slides the sheath 6 away from the syringe about an inch and places the syringe body 4 in the syringe support brackets 41 and the plunger body flange 36 in the plunger support bracket 45. Syringe retainers 42 and plunger retainer 46 are then snapped closed and the casing cover 82 is closed and locked by pushing down on the top of the casing cover until it snaps shut. Sheath 6 is then slid along the needle toward the apparatus and sheath luer-lock hub 11 is locked onto the casing luer-lock connection 81.

Sheath positioning handle 14 is then snapped onto the sheath handle attachment area 12 at a position appropriate for the operator's hand size and in the direction of right or left-hand operation, as appropriate.

The operator then positions the tip of the sheath and needle trans-rectally proximate to the target area, palpating with his or her finger tip to precisely locate the target area. Automatic aspiration is thereafter initiated by closing the safety switch 115 and depressing trigger 86.

Upon depressing the trigger, the first solenoid 70 is energized thereby causing the drive bar 57 to move forward against the bias of springs 61 until it abuts drive bar stop screw 69, actuating front drive bar sensor 125. Forward movement of the drive bar 57 causes the entire carriage assembly, including motor 55, gearbox 56, lead screw 50, end plate 59, syringe support brackets 41, syringe carriage 40, plunger 5, plunger support bracket 45, syringe 4, stylet 3, and needle 2, to move forward to a position corresponding to the "B" position in FIG. 1. The control circuit further energizes detent solenoid 66. The upper surface of detent 65 is cammed so that rear syringe support bracket 41 can easily move past the detent in the forward direction, but cannot move rearward over the detent. The forward excursion of the carriage assembly causes the needle tip 19 (and stylet tip 26) to emerge from the sheath and penetrate the target area until it reaches the far end of the target area, in this example 20 mm. The control circuit (described below) thereafter deenergizes main solenoid 70 so that the carriage assembly retracts under the bias of springs 61. Because detent 65 is driven to its uppermost position by the detent solenoid 66, complete retraction of the carriage is prevented. The carriage thus retracts to the "C" position in FIG. 1, in this instance 5 mm, so that the tips of the needle and stylet are now at the near end of the target area. Rear drive bar sensor 126 is actuated when the carriage reaches the semi-retracted or "C" position.

When the carriage is in the semi-retracted or "C" position, the motor 55 is activated by the control circuit so as to rotatably drive lead screw 50 through the gear box 56 to retract the second movable unit (defined by plunger support bracket 45, plunger 5 and stylet 3), with respect to the first movable unit (defined by syringe support brackets 41, syringe carriage 40, syringe 4 and needle 2). Retraction of the second movable unit deactivates plunger front limit sensor 127.

Retraction of the plunger 5 causes the stylet 3 to retract with respect to the needle 2. Consequently, a passage is formed from the tip of the needle 19 to the sample storage portion 20 of the needle. Additionally, the retraction of the plunger head 33 with respect to the syringe 4 results in a partial vacuum in chamber 34 creating suction at the tip of the needle. When the plunger is fully withdrawn, plunger rear limit sensor 128 is activated, thereby causing the control circuit to turn off motor 55.

The control circuit thereafter causes the carriage to reciprocate so that sample is collected. Reciprocation is achieved by alternately energizing and deenergizing the main solenoid 70 so that the carriage assembly is alternately moved forward by the solenoid and rearwardly by springs 61. After a predetermined (programmable) number of reciprocations has been sensed by the control circuit, the control circuit ends the reciprocation cycle and activates the motor 55 in reverse so that plunger 5 and stylet 3 are returned to their original position. As the stylet is returned to its original position, the passage between the tip of the needle and the sample storage portion of the needle is once again sealed to prevent contamination of the collected sample upon needle withdrawal.

When plunger 5 is completely returned to its original position, plunger carriage front limit sensor 127 is once again actuated, turning off motor 55. Detent solenoid 66 is also deenergized, such that detent 65 withdraws, permitting the carriage to return to the fully retracted or "A" position (FIG. 1) under the bias force of springs 61, thus completing the aspiration procedure.

Upon completion of the procedure, the sheath is withdrawn from the rectum, the sheath guide is removed from the index finger and the glove on that hand is removed and discarded. The sheath luer-lock hub 11 is removed from the casing luer-lock 81, and the cover of the device is opened by pushing the cover release button 83. The syringe and plunger retainers 42, 46 are similarly opened and the syringe assembly is removed from the device. The needle luer-lock hub 18 is then disengaged from the syringe luer-lock 31, and the syringe with the stylet 3 are separated from the needle and discarded. A second syringe filled with air is then attached to the needle luer-lock hub 18. The sheath is then withdrawn and discarded and the cell sample in the needle is expressed onto a glass microscope slide for cytological examination.

FIG. 17 diagramatically illustrates the control sequence of the main solenoid 70, the detent solenoid 66, the motor 55, the red LED 134, and the green LED 131 during normal operation. More specifically, FIG. 17 shows a preferred control sequence wherein electrical current (shown as a solid black line) is provided to the various components which are listed on the vertical axis at selected times during a normal cycle illustrated along the horizontal time axis.

As shown in FIG. 17, when the apparatus is ready for operation (after the power switch 110 is turned on), a steady green LED 131 lights. Pulling the trigger 86 (point "a" in FIG. 17) begins the cycle, causing red LED 134 to light and green LED 131 to go off. The trigger also actuates main solenoid 70 and detent solenoid 66. Thereafter, the main solenoid 70 is turned off, and the motor 55 is actuated in a clockwise direction by motor control 153 (discussed below) at point "b". At point "c", the motor 55 is turned off and the first solenoid 70 receives a pre-programmed number of current pulses. At point "d", the motor 55 is turned on in a counterclockwise direction via motor control 154 (discussed below) to return the plunger to the full forward position. Finally, at point "e", the detent solenoid 66 is turned off, the red LED 134 is turned off, and the rotation of the motor 55 in the counterclockwise direction is stopped, thus ending the cycle.

From the above description, it should be apparent that operation of the aforementioned components in the above sequence results in the performance of the fine needle aspiration procedure. In particular, activation of the main solenoid 70 causes the carriage assembly to move forward to the "B" position (FIG. 1) while the red LED 134 indicates to the operator that the cycle is in progress.

When the main solenoid 70 is turned off and the detent solenoid 66 is on, the carriage assembly returns to the semi-retracted "C" position (FIG. 1) under the bias of the springs 61 until detent 65 is engaged. Simultaneously, the motor turns counterclockwise to retract the plunger and stylet thereby opening a passage between the tip of the needle and the cell sample storage portion of the needle and creating suction to draw sample material past the tip of the needle into the cell sample storage portion of the needle.

When the plunger and stylet are fully retracted the motor is turned off and the main solenoid is pulsed to reciprocate the needle between "B" and "C" positions (corresponding to FIGS. 1d and 1e) a predetermined number of times.

After completion of the predetermined number of reciprocations, the motor is turned counterclockwise to return the plunger and stylet to the closed position. After the plunger and stylet are returned to the closed position, the detent solenoid 66 is turned off so that the carriage is returned to the initial or "A" position (FIG. 1) by the springs. Red LED 134 is then turned off, informing the operator that the operation is complete.

Having thus described the mechanical operation of the first embodiment of the invention, set forth below is a description of the structure and operation of a solid-state logic circuit for controlling the first embodiment of the invention.

Figure 18:
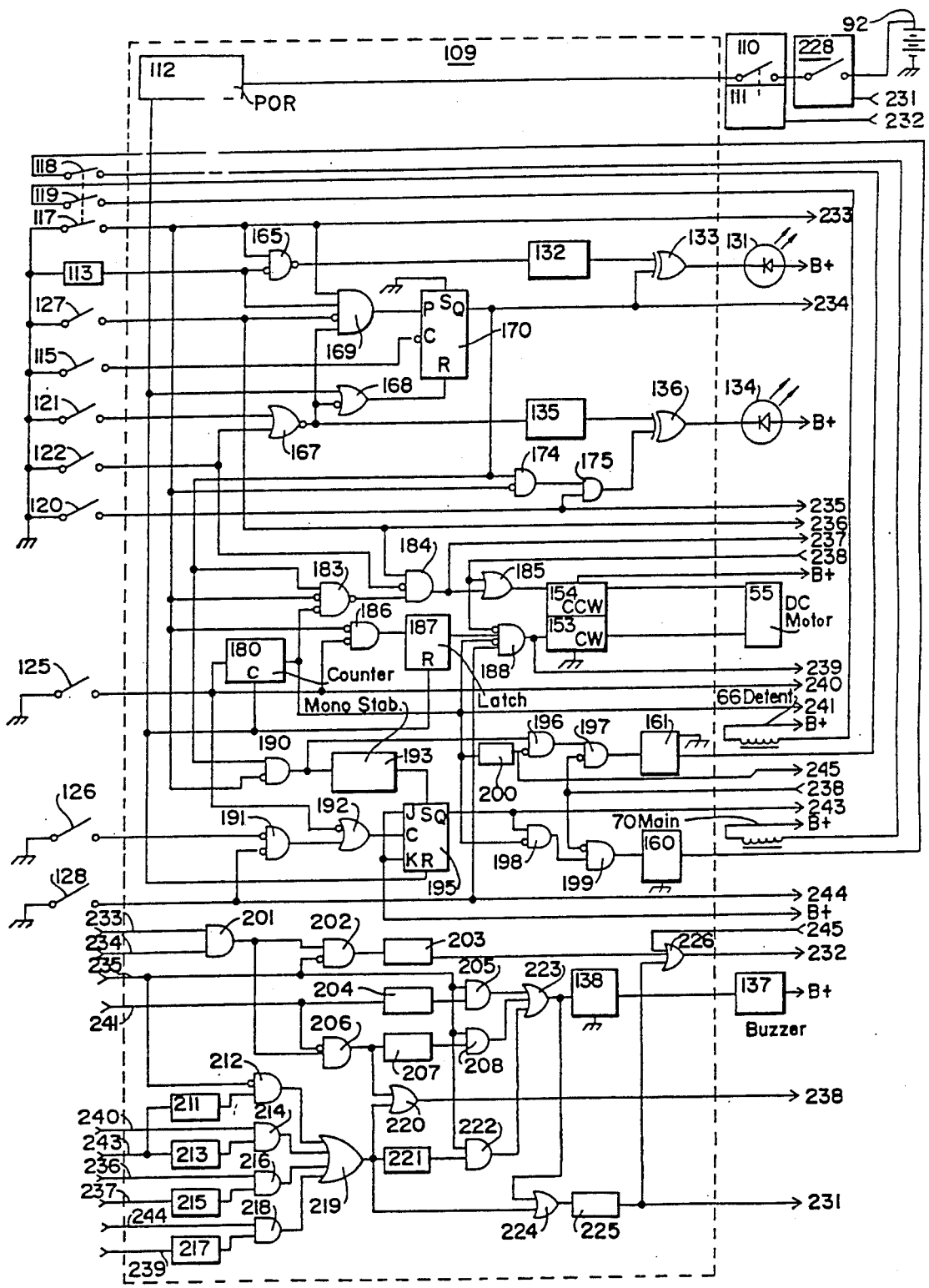
FIG. 18 is a control circuit for the first embodiment of the present invention.

As shown in FIG. 18, electronic control circuit 109 of the first preferred embodiment of the fine needle aspiration device is provided to control the orderly operation of the various electrical indicators and electromechanical devices of the invention. Battery 92 is provided as a power source. Manual push-on push-off type power switch 110 is provided for connecting power from battery 92 to the electronic logic elements of control circuit 109. Power-on-reset (POR) circuit 112 is provided that emits a momentary signal of level high (H) when power switch 110 is closed. Three ganged switches 117-119, each a single-pole single-throw spring-loaded normally-open debounced switch, are provided to initiate the biopsy operation when they are closed and to safely terminate the operation in progress when they are opened. Operation control switch 117 emits a signal of level low (L) when closed and a signal of level H when opened. Main solenoid cut-off switch 118 connects main solenoid control circuit 160 and main solenoid 70 when closed and disconnects them when opened. Detent solenoid cut-off switch 119 connects detent solenoid control circuit 161 and detent solenoid 66 when closed and disconnects them when opened.

Battery voltage level sensor 113 indicates the amount of power remaining in battery 92 by emitting a signal of level H when the voltage on battery 92 is sufficient to operate the device reliably, and a signal of level L otherwise. NAND gate 165 is provided for emitting an inverted logical product between the "not" of battery voltage level sensor 113 output and the output from operation control switch 117. Green flashing control circuit 132, which is an astable gated oscillator circuit, is provided that outputs a continuously oscillating signal between level H and level L in response to an input signal of level L, and outputs a signal of level H in response to an input signal of level H. The output of NAND gate 165 is connected to the input of green flashing control circuit 132.

Safety switch 115 is a single-pole single-throw spring-loaded momentary normally-open push-button type debounced switch which emits a signal of level L when closed and a signal of level H when open. Single-pole single-throw debounced sheath switch 121 emits a signal of level L when closed and a signal of level H when open. Cover switch 122, which is a single-pole single-throw debounced switch, emits a signal of level L when closed and a signal of level H when open. Debounced front plunger limit sensor 127 emits a signal of level L when activated by plunger support bracket 45 being in its forwardmost position as shown in FIG. 13, and emits a signal of level H when the plunger support bracket 45 is in any other position. NOR gate 167 is provided that emits an inverted logical sum between the output of the sheath switch 121 and the cover switch 122. Four input AND gate 169 is provided that emits a logical product between the output of operation control switch 117, the output of battery voltage level sensor 113, the "not" of the output of front plunger limit sensor 127 and the output of NOR gate 167. OR gate 168 is provided that emits a logical sum between the "not" of the output of NOR gate 167 and the output of POR circuit 112. Flip-flop 170 is a clocked D-type flip-flop and emits a signal at the Q output, the state of which is dependent on the signal from the output of AND gate 169 connected to the Data input line D, the "not" of the output from safety switch 115 connected to the Clock input line C, the output of OR gate 168 connected to the Reset input line R, and the Set input S which is held at a signal level of L. XOR gate 133 is provided that emits a logical "exclusive-or" between the output of flip-flop 170 and green flashing control circuit 132. Green LED 131 can be in one of three states: off, steady on or flashing on and off.

Red flashing control circuit 135, an astable gated oscillator circuit, is provided that outputs a continuously oscillating signal between level H and level L in response to an input signal of level L, and outputs a signal of level H in response to an input signal of level H. The output of NOR gate 167 is connected to the input of flashing control circuit 135. Origin sensor 120 is provided which emits a signal of level L when it is closed and it is closed if and only if the lead screw support bar end plate 59 is in close proximity to it. AND gate 174 is provided for emitting the logical product between the output of flip-flop 170 and the "not" from the output of operation control switch 117. AND gate 175 is provided for emitting the logical product between the output of origin sensor 120 and the output of AND gate 174. XOR gate 136 is provided for emitting a logial "exclusive-or" between the output of AND gate 175 and flashing control circuit 135. Red LED 134 can be in one of three states: off, steady-on or flashing on and off.

Front drive bar sensor 125, which is a debounced switch, emits a signal of level L when it is closed and it is closed if and only if in close proximity with syringe carriage drive bar 57. Debounced rear syringe carriage sensor 126 emits a signal of level L when it is closed and it is closed if and only if the bottom end of syringe carriage 40 is in close proximity to it. Debounced rear plunger limit sensor 128 emits a signal of level L when it is closed and it is closed if and only if plunger support bracket 45 is in close proximity to it.

Adjustable counter circuit 180 is provided to count for a programmable number of times input signal changes from level H to level L and for emitting a signal of level L or H. The preferable range of the programmable number is between one and one hundred, and can be programmed by micro-switches (not shown). Any count below the programmed number causes adjustable counter circuit 180 to emit a signal of level L. Any count at or above the programmed number causes adjustable counter circuit 180 to emit a signal of level H. The output of front drive bar sensor 125 is connected to the input of adjustable counter circuit 180. The output of POR circuit 112 is connected to the Reset input C of adjustable counter circuit 180. A signal of level H at the Reset input will cause adjustable counter 180 to reset the count to zero and to emit a signal of level L.

Three input NAND gate 183 is provided for emitting the logical product between the "not" of the output of operational control switch 117, the output of flip-flop 170 and the "not" of the output of adjustable counter circuit 180. Three input AND gate 184 is provided for emitting the logical product between the output of front plunger limit sensor 127, the "not" of the output of cover switch 121 and the output of NAND gate 183. OR gate 185 is provided for emitting the logical sum between the output of OR gate 220 on line 238 and the output of AND gate 184. Motor counter-clockwise control circuit 154 is provided that outputs the proper voltage and current levels for turning motor 55 in a counter-clockwise direction. The output signal of OR gate 185 is input to the motor counterclockwise control circuit 154 which is activated by an input signal of level H and turned off by an input signal of level L.

AND gate 186 is provided for emitting the logical product between the "not" of the output of operation control switch 117 and the "not" of the output of front drive bar sensor 125. Latch 187 is provided for emitting a constant signal of level H in response to a momentary signal of level H at the Set input. The output from AND gate 186 is connected to the Set input of latch 187. The output of POR circuit 112 is connected to the Reset input of latch 187. A momentary signal of level H at the Reset input R of latch 187 resets the output signal to level L. Four input AND gate 188 is provided for emitting the logical product between the "not" of the output of OR gate 220 on line 238, the output of latch 187, the output of rear plunger limit sensor 128 and the "not" of the output of adjustable counter circuit 180. Motor clockwise control circuit 153 is provided that outputs the proper voltage and current levels for turning the motor 55 in a clockwise direction. The output signal of AND gate 188 is input to motor clockwise control circuit 153 which is activated by an input signal of level H and turned off by an input signal of level L.

AND gate 190 is provided for emitting the logical product between the output of flip-flop 170 and the "not" of the output of operation control switch 117. Monostable 193 is provided for emitting a momentary signal pulse of level H in response to the signal level change from L to H of the output of AND gate 190. AND gate 191 is provided for emitting a logical product between the "not" of the output of rear drive bar sensor 126 and the "not" of the output of rear plunger carriage limit sensor 128. OR gate 192 is provided for emitting the logical sum between the output of AND gate 191 and the "not" of the output of front drive sensor 125.

Flip-flop 195 is a clocked J-K type flip-flop and is provided for emitting a signal at the Q output dependent on the state of the signal output by AND gate 192 connected to the Clock input line, the signal output by monostable 193 connected to the Set input line, the signal output by POR circuit 112 connected to the Reset input line, and the J and K input lines held at a signal level H. With the J and K input lines held at signal level H, a signal level change from L to H at the Clock input will cause the Q output to toggle. A signal level of L at the Set or the Reset input has no effect on the Q output. A signal level of H at the Set input immediately forces the Q output to a signal of level H. A signal of level H at the Reset input immediately forces the Q output to a signal of level L.

Delay circuit 200 is provided for delaying the output of adjustable counter 180. The time period of delay circuit 200 is set equal to (or greater than) the time it takes for the motor 55 to run counter-clockwise sufficient to fully return the plunger 5 to the closed or forwardmost position. In other words, the time period of delay circuit 200 is equal to or greater than the time measured between plunger rear limit sensor 128 opening, and plunger front limit sensor 127 closing, during normal operation. AND gate 196 is provided for emitting the logical product between the output of AND gate 190 and the "not" of the output of delay circuit 200. AND gate 197 is provided for emitting the logical product between the output of AND gate 196 and the "not" of the output of OR gate 220 on line 238. Detent solenoid control circuit 161 is provided for emitting the proper current and voltage level to control detent solenoid 66 in response to the signal at the output of AND gate 197. A signal of level H input to detent solenoid control circuit 161 turns detent solenoid 66 on and a signal of level L turns it off.

The output of delay circuit 200 is also applied, through line 245, as an input to OR gate 226.

AND gate 198 is provided for emitting the logical product between the output of flip-flop 195 and the "not" of the output of adjustable counter circuit 180. AND gate 199 is provided for emitting the logical product between the output of AND gate 198 and the "not" of the output of OR gate 220 on line 238. Main solenoid control circuit 160 is provided for emitting the proper current and voltage level to control main solenoid 70 in response to the output of AND gate 199. A signal of level H input to main solenoid control circuit 160 turns main solenoid 70 on and a signal of level L turns it off.

AND gate 201 is provided for emitting the logical product between the output of operation control switch 117 on line 233 and the output of flip-flop 170 on line 234. AND gate 202 is provided for emitting the logical product between the output of AND gate 201 and the "not" of the output of origin switch 120 on line 235. Delay circuit 203 is provided for emitting the same signal level as the output of AND circuit 202 after a time delay. Delay circuit 204 is provided for emitting the same signal level as the output of adjustable counter 180 via line 241 after a time delay. AND gate 205 is provided for emitting the logical product between the output of origin sensor 120 on line 235 and the output of delay circuit 204. AND gate 206 is provided for emitting the logical product between the "not" of the output of adjustable counter 180 on line 241 and the output of AND gate 201. Delay circuit 207 is provided for emitting the same signal level as the output of AND gate 206 after a time delay. AND gate 208 is provided for emitting the logical product between the output of origin sensor 120 on line 235 and the output of delay circuit 207. Delay circuit 211 is provided for emitting the same signal level as the output of flip-flop 195 on line 243 after a time delay. AND gate 212 is provided for emitting the logical product of the "not" of the output of origin sensor 120 on line 235 and the output of delay circuit 211. Delay circuit 213 is provided for emitting the same signal level as the output of flip-flop 195 on line 243, after a time delay. AND gate 214 is provided for emitting the logical product of the output of front drive bar sensor 125 on line 240 and the output of delay circuit 213. Delay circuit 215 is provided which emits the same signal level as the output of AND circuit 184 on line 237, after a time delay. AND gate 216 is provided for emitting the logical product of the output of front limit sensor 127 on line 236 and the output of delay circuit 215. Delay circuit 217 is provided which emits the same signal level as the output of AND gate 188 on line 239 after a time delay. AND gate 218 is provided for emitting the logical product of the output of the rear limit sensor 128 on line 244 and delay circuit 217.

Four input OR gate 219 is provided for emitting the logical sum between the outputs of AND gates 212, 214, 216 and 218. Two input OR gate 220 is provided for emitting, on line 238, the logical sum between the outputs of OR gate 219 and AND gate 206. Delay circuit 221 is provided for emitting the same signal level as the output of OR gate 219, after a time delay. AND gate 222 is provided for emitting the logical product of the output of delay circuit 221 and origin sensor 120 on line 235. Three input OR gate 223 is provided for emitting the logical sum between the outputs of the AND gates 205, 208 and 222. OR gate 224 is provided for emitting the logical sum of the outputs of OR gates 219 and 223. Delay circuit 225 is provided for emitting, on line 231, the same signal level as the output of OR gate 224 after a time delay. Three input OR gate 226 is provided for emitting on line 232 the logical sum of the outputs of delay circuits 200 on line 245, 203 and 225.

Breaker 111 is provided for opening power switch 110 disconnecting power to electronic control circuit 109 in response to a signal of level H from the output of OR gate 226 on line 232. Breaker 111 is mechanically linked to power switch 110 so that closing power switch 110 also closes breaker 111.

Fault indicating breaker 228 is provided for disconnecting the power to electronic control circuit 109 in response to a signal of level H from the output of delay circuit 225 on line 231.

Buzzer control circuit 138 is provided for emitting the proper current and voltage for sounding buzzer 137 in response to a signal of level H output by OR gate 223.

Having thus described the structure of the control circuit of the first embodiment of the invention, the operation of the control circuit will now be described with reference to the figures.

The fine-needle aspiration apparatus is controlled electronically by the state of the manual switches and the position detecting sensors. For the apparatus to function properly the operator must open or close the switches in a predetermined order following an instruction procedure. The apparatus is designed not to permit operation if certain safety conditions are not met. Once in operation, the apparatus is designed to safely terminate operation should either the operator decide to abort the operation or if an electromechanical fault or jam occurs. The description of the electronic control of the apparatus is divided below into six function areas: Initialization, Safety Conditions Checked, Operation, Normal End of Operation, Terminating an Operation by Releasing the Trigger, and Failsafe Shutdown of Operation Due to an Electromechanical Fault.

(i) Initialization

When power switch 110 is closed, battery 92 is connected to electronic control circuit 109 providing power to the electronic logic elements in electronic control circuit 109. The closing of power switch 110 immediately triggers POR circuit 112 which sends a momentary signal of level H to the following: the Clear input C of adjustable counter 180 which sets the count to zero and causes the output to be a signal of level L; the Reset input R of latch 187 causing the output to be a signal of level L, the Reset input R of flip-flop 195 causing the Q output to be a signal of level L, and, by way of OR gate 168, the Reset input R of flip-flop 170 causing the Q output to be a signal of level L.

All switches and sensors are debounced. Excluding switches 110, 228, 118 and 119, all switches and sensors, when closed, connect the respective signal lines to ground level L. When these switches are open, the respective signal lines, which are connected through current limiting resistors (not shown) to B+, are pulled to level H. In other words, an open switch or sensor emits a signal of level H; a closed switch or sensor emits a signal of level L.

The normal initial states of all switches, sensors, indicators, and electromechanical devices after power switch 110 is closed are set forth in Table I below:

TABLE I

110: power switch closed
118: main solenoid cutoff switch open
119: detent solenoid cutoff switch open
117: operation control switch open, emits signal of level H
113: battery voltage level sensor emits a signal of level H
115: safety switch open, emits a signal of level H
121: sheath switch closed, emits a signal of level L
122: cover switch closed, emits a signal of level L
120: origin sensor closed, emits a signal of level L
125: front drive bar sensor open, emits a signal of level H
126: rear drive bar sensor open, emits a signal of level H
127: front plunger limit sensor closed, emits a signal of level L
128: rear plunger limit sensor open, emits a signal of level H
131: green LED off
134: red LED off
55: plunger motor off
66: detent solenoid off
70: main solenoid off
137: buzzer off
228: fault indicating breaker closed (ii) Safety Conditions Checked After power switch 110 is closed but before operation control switch 117 is closed, if battery voltage level sensor 113 is emitting a signal of level L indicating low battery voltage, NAND gate 165 will emit a signal of level L to green flashing control circuit 132 so that it goes into its flashing mode emitting a signal oscillating between level L and level H. The signal passes through XOR gate thereby flashing green LED 131 so the operator can be alerted that the battery voltage is low. If battery voltage level sensor 113 begins emitting a signal of level L after operation control switch 117 is closed so that it is emitting a signal of level L, then NAND gate 165 will emit a signal of level H which causes green flashing control circuit 132 to emit a signal of level H which functions to prevent green LED 131 from flashing so that the operator will not be distracted during an operation. Battery voltage level sensor 113 is adjusted so that when it detects that the battery voltage is low there will still be enough voltage to reliably complete the current operation.

The signal level output by XOR gate 133 is input to green LED 131 and determines which of the three states green LED 131 is in: a signal of level H turns green LED 131 off which indicates the apparatus is not ready and cannot be operated until certain safety conditions are met, a signal of level L turns green LED 131 steady on which indicates the apparatus is ready and will go into operation when operation control switch 117 is closed, or a signal that oscillates between level L and H causing green LED 131 to flash on and off which alerts the operator that the voltage level in battery 92 is low and that battery 92 needs to be charged or replaced.

Before the device can be made to operate, the following safety conditions must be satisfied: trigger 86 must not be squeezed, that is, the operation control switch 117 is open, battery 92 must be charged so that battery voltage level sensor 113 emits a signal of level H, front plunger carriage limit sensor 127 must be closed, safety switch 115 must be open, sheath switch 121 must be closed and cover switch 122 must be closed. Only when these conditions are all met will flip-flop 170 emit a signal of level H causing green LED 131 to turn steady on when the safety switch 115 is momentarily closed. After the power-on initialization, but before the operation begins, if any safety conditions are not satisfied, then flip-flop 170 will only emit a signal of level L when safety switch 115 is momentarily closed.

When safety switch 115 is activated the switch momentarily changes from open to closed which causes the output signal level to change from H to L. This signal is inverted and applied to the Clock input C of flip-flop 170 causing the same signal level of the output of AND gate 169 at the Data input D of flip-flop 170 to be emitted at the Q output of flip-flop 170.

In this regard, by checking the signal levels input to AND gate 169, the safety condition of the device is determined and indicated by the output of AND gate 169: an output signal level of L indicates the device is not ready; an output signal level of H indicates the device is ready.

A signal of level L output by operation control switch 117 prevents the device from going into operation immediately if safety switch 115 is closed after closure of operation control switch 117. For example, if the operator is squeezing trigger 86 when safety switch 115 is activated, the operation will not start.

A signal of level L output by battery voltage level sensor 113 indicates that the voltage of battery 92 is too low, and hence the apparatus is disabled.

A signal of level H output by front plunger limit sensor 127 indicates that plunger carriage 45 is not in its initial position, either because carriage 45 did not return to its initial position after a previous operation of the apparatus or because an electromechanical failure occurred requiring that the apparatus not be operated.

A signal of level L output by safety switch 115 indicates that safety switch 115 is being held closed. Because flip-flop 170 will only output the signal level at the Data input D on a Clock input signal change from level L to level H, it is necessary to release (open) the safety switch 115 before pushing it closed. In other words, this safety condition prevents the apparatus from being operative accidentally due to safety switch 115 being disabled, stuck closed, taped closed or manually held closed. Furthermore, if any of the safety conditions are not satisfied and safety switch 115 is pushed closed, after the problem is detected and corrected, safety switch 115 still must be released and pushed again.

Locking sheath luer-lock hub 11 properly to casing luer-lock connection 81 closes sheath switch 121. Closing hinged casing cover 82 so that it snaps into the locked position closes cover switch 122. A signal of level H output by sheath switch 121 or cover switch 122, or both, is logically summed by NOR gate 167, the level L output of which subsequently prevents the apparatus from being ready. This prevents unsafe operation of the apparatus with sheath luer-lock hub 11 improperly attached to casing luer-lock connection 81 or with hinged casing cover 82 open or even partly open.

Further, if all the safety conditions are met and safety switch 115 is closed momentarily and green LED 131 comes on indicating that the apparatus is ready, and if then the operator were to open sheath luer-lock hub 11 or hinged casing cover 82, which would open sheath switch 121 or open cover switch 122, then OR gate 168 would send a signal of level H to the Reset input of flip-flop 170 which would immediately output a signal of level L making the apparatus not ready and turning off green LED 131. To make the apparatus ready again in this case it is necessary to start over; i.e., lock sheath luer-lock hub 11 properly to casing luer-lock 81 to close sheath switch 121, and close hinged casing cover 82 into the snapped locked position to close cover switch 122, and meet all the other safety conditions before again closing safety switch 115 momentarily.

Further, whenever power switch 110 is closed and either sheath switch 121 or cover switch 122 is open, the output of NOR gate 167 will be a signal of level L causing red flashing control circuit 135 to go into its flashing mode emitting a signal oscillating between level L and level H which passes through XOR gate 136 thereby flashing red LED 134 so that the operator can be alerted that sheath hub 11 or hinged casing cover 82 is not properly secured or shut. The signal level output by XOR gate 136 is input to red LED 134 and determines which of the three states it is in: a signal of level H turns red LED 134 off which indicates the operation has not begun or has been completed or has been terminated, a signal of level L turns red LED 134 steady on which indicates that the operation has begun and is in progress, or a signal that oscillates between level L and H causing red LED 134 to flash on and off which indicates that either cover switch 122 or sheath switch 121 has not been closed.

(iii) Operation

After all of the safety conditions are satisfied, with the output of flip-flop 170 emitting a signal of level H and green LED 131 on steady, the apparatus is ready for operation. When the operator has oriented and positioned the tip of sheath 9 correctly as described above, the operation is commenced by squeezing trigger 86 which closes detent solenoid cutoff switch 119, main solenoid cutoff switch 118 and operation control switch 117. At this point the operation of the apparatus is automatic for so long as the operator continues squeezing trigger 86, thus keeping the operation control switch 117 closed. The sequence of events is as follows with reference to FIGS. 1a-1f and 13-18.

AND gates 174 and 190 then emit signals of level H. Monostable 193 emits a momentary signal of level H which triggers the Set input of flip-flop 195 which outputs a signal of level H. This causes the output of AND gate 198 to be a signal of level H which makes the output of AND gate 199 a signal of level H. This turns main solenoid control circuit 160 on and energizes main solenoid 70 which, in turn, draws syringe carriage drive bar 57 forward and with it the entire carriage assembly, including: syringe carriage 40, syringe support brackets 41, plunger support bracket 45, motor 55, gear box 56, lead screw support bar 58, lead screw support bar end plate 59, syringe retainers 42, plunger retainers 46, syringe body 4, plunger 5, stylet 3 and needle 2. Also, movement of drive bar 57 pushes needle tip 19 forward out of the tip of sheath 9 to its full present forward excusion as shown in FIG. 1b.

As syringe carriage drive bar 57 moves forward it compresses syringe carriage helical return springs 61, and opens origin sensor 120 which causes AND gate 175 to emit a signal of level H which causes XOR gate 136 to emit a signal of level L which turns red LED 134 on steady alerting the operator that the operation has begun and is in progress. As syringe carriage drive bar 57 moves forward, the rear syringe support bracket 41 passes over and forward of detent 65 and passes over and forward of rear drive bar sensor 126 closing it momentarily and then opening it. This signal level change causes no change in the output of AND gate 191 because plunger rear limit sensor 128 is open at this time.

Also, when AND gate 190 emits a signal of level H, AND gate 196 emits a signal of level H which, in turn, makes detent solenoid control circuit 161 turn on thereby energizing detent solenoid 66 which draws detent 65 upwards.

As syringe carriage drive bar 57 continues to move forward it makes contact with drive bar forward stop screw 69 stopping its forward motion in the full forward excursion position as shown in FIG. 1b. Also, in this position syringe carriage drive bar 57 is detected by front drive bar sensor 125 causing front driver bar sensor 125 to close emitting a signal of level L. This causes the output of OR gate 192 to go from a signal of level L to H which causes flip-flop 195 to change states, producing a signal of level L. This causes AND gate 198 to output a signal of level L which causes AND gate 199 to output a signal of level L which, in turn, causes main solenoid control circuit 160 to turn off main solenoid 70.

Also, at the time when front drive bar sensor 125 closes, it emits a signal level change from H to L which causes adjustable counter 180 to increment its internal counter from zero to one. However, until counter 180 reaches the programmed number, it continues to emit a signal of level L.

Also, at the time when sensor 125 emits a signal of level L, AND gate 186 emits a signal of level H which causes latch 187 to change from L to H which in turn causes AND gate 188 to emit a signal of level H. This causes the motor clockwise control circuit 153 to turn on and to turn motor 55 in a clockwise direction which, by means of gear box 56, turns plunger lead screw 50 in a clockwise direction thereby moving plunger support bracket 45 rearward. This begins retracting plunger 5 and stylet 3, respectively, from syringe body 4 and needle 2. Retraction of plunger 5 creates low pressure within syringe body 4. When stylet 3 clears the narrow diameter portion 16 of needle 2, sample is drawn into needle tip 19.

Picking up from the point in time when main solenoid 70 is turned off, syringe carriage helical return springs 61, which have been compressed, now release their stored energy and push syringe carriage 40 rearward along with the entire carriage assembly. Consequently, needle 2 is partly withdrawn back into sheath 6. As syringe carriage drive bar 57 moves rearward, front drive bar sensor 125 opens which causes OR gate 192 to emit a signal of level L. Syringe carriage drive bar 57 continues to be pushed rearward by return springs 61 until the lower end of rear syringe support bracket 41 is stopped by detent 65. In this intermediate position, rear drive bar sensor 126 detects syringe carriage lower end 41 and closes, emitting a signal of level L.

The rearward movement of plunger support bracket 45 causes plunger front limit sensor 127 to open thereby emitting a signal of H. When plunger support bracket 45 reaches the proximity of lead screw support bar end plate 59, plunger rear limit sensor 128 detects the position of plunger support bracket 45 and closes emitting a signal L. This causes AND gate 188 to emit a signal of level L which causes motor clockwise control circuit 153 to turn off motor 55 which stops the rearward motion of plunger support bracket 45 as shown in FIG. 1d. When plunger rear limit sensor 128 closes it also causes AND gate 191 to emit a signal of level H.

Next begins a reciprocation cycle. The signal of level H at the output of AND gate 191 causes OR gate 192 to change from signal level L to H which causes the Clock input C of flip-flop 195 to toggle the Q output to a signal of level H. This causes AND gate 198 to emit a signal of level H which causes AND gate 199 to emit a signal of level H which turns main solenoid control circuit 160 on and energizes main solenoid 70. This draws syringe carriage drive bar 57 forward and with it the entire carriage assembly, and pushes needle tip 19 forward. As syringe carriage drive bar 57 moves forward it compresses syringe carriage helical return springs 61, and it opens rear drive bar sensor 126 which causes AND gate 191 to emit a signal of level L. This causes OR gate 192 to emit a signal of level L.

Figure 1E:
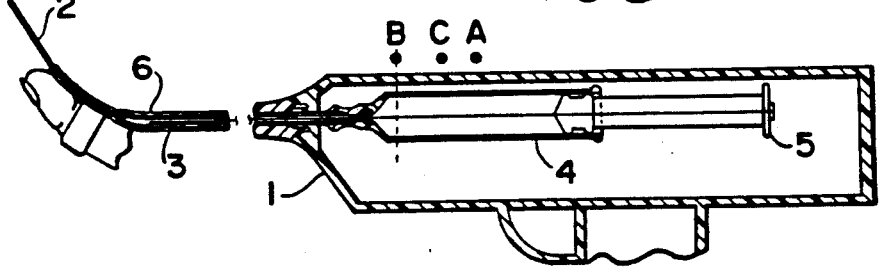
Figure 1F:
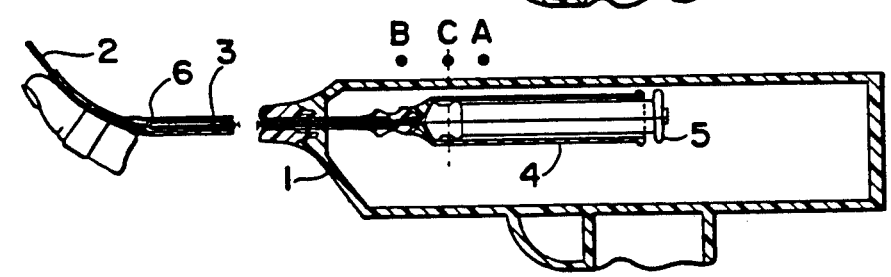

As syringe carriage drive bar 57 continues to move forward it makes contact with drive bar forward stop screw 69 stopping its forward motion in the full forward excursion position as shown in FIG. 1e. Also, in this position syringe carriage drive bar 57 is detected by front drive bar sensor 125 causing front drive bar sensor 125 to close emitting a signal of level L. This causes OR gate 192 to emit a signal of level H which causes flip-flop 195 to toggle and to produce a signal of level L. This causes AND gate 198 to output a signal of level L which causes AND gate 199 to output a signal of level L which, in turn, causes main solenoid control circuit 160 to turn off main solenoid 70.

Also, at the time when front drive bar sensor 125 closes, it emits a signal level change from H to L which causes adjustable counter 180 to increment from one to two. However, because it has not reached the programmed number, adjustable counter 180 continues to emit a signal of level L.

When main solenoid 70 is turned off, syringe carriage helical return springs 61 which have been compressed now release their stored energy and push syringe carriage 40 rearward along with the entire carriage assembly. Needle tip 19 is again partly withdrawn back into the tip of sheath 9. As syringe carriage drive bar 57 moves rearward, front drive bar sensor 125 opens which causes AND gate 192 to emit a signal of level L. Syringe carriage drive bar 57 continues to be pushed rearward by return springs 61 until the lower end of rear syringe support bracket 41 is stopped by detent 65. In this position, rear drive bar sensor 126 detects rear syringe support bracket 41 and closes emitting a signal of level L which causes AND gate 191 to emit a signal of level H.

At this point the adjustable counter 180 is at count two and the apparatus is about to repeat the series of events included in the reciprocation cycle. Each time the apparatus completes a cycle the count of adjustable counter 180 is incremented. When the count equals the programmed number, adjustable counter 180 emits a signal of level H and the normal end of operation procedures and functions begin.

(iv) Normal End of Operation

When adjustable counter 180 emits a signal of level H this causes NAND gate 183 to emit a signal of level H which causes AND gate 184 to emit a signal of level H. This causes OR gate 185 to emit a signal of level H which, in turn, causes motor counter-clockwise control circuit 154 to turn plunger carriage motor 55 counter-clockwise which, by means of gear box 56, turns plunger lead screw 50 in a counterclockwise direction which moves plunger support bracket 45 forward pushing plunger 5 forward into the syringe body 4, and pushing stylet 3 forward into needle 2 occluding the needle. Plunger 5 must return back into syringe body 4 so that the low pressure will be relieved and needle 2 will be occluded by stylet 3 to prevent contamination of the sample upon withdrawal of the needle from the target area.

As plunger carriage motor 55 continues to turn counterclockwise pushing plunger support bracket 45 forward, plunger rear limit sensor 128 opens and then plunger front limit sensor 127 closes which causes AND gate 184 to emit a signal of level L. This causes OR gate 185 to emit a signal of level L which causes motor counter-clockwise control circuit 154 to turn off plunger carriage motor 55. This stops the motion of plunger carriage lead screw 50 and the forward motion of plunger support bracket 45 and plunger 5.

Simultaneously, when adjustable counter 180 emits a signal of level H, AND gate 198 is caused to emit a signal of level L which causes AND gate 199 to emit a signal of level L. This causes main solenoid control circuit 160 to turn off main solenoid 70 which allows syringe carriage helical return springs 61 to push syringe carriage 40 rearward opening front drive bar sensor 125, and then closing rear drive bar sensor 126 and stopping rearward motion when the lower end of syringe 41 support bracket contacts detent 65.

Simultaneously, when adjustable counter 180 emits a signal of level H, delay circuit 200 is caused to begin its delay period for a length of time equal to or greater than the time it takes for plunger carriage motor 55 to push plunger support bracket 45 forward until plunger front limit sensor 127 emits a signal of level L. At the end of the delay period, delay 200 emits a signal of level H which causes AND gate 196 to emit a signal of level L which, in turn, causes AND gate 197 to emit a signal of level L. This causes detent solenoid control circuit 161 to turn off detent solenoid 66 which allows detent spring 67 to draw detent 65 downward. This allows syringe carriage helical return springs 61 to push syringe carriage 40 rearward to the original starting position illustrated in FIG. 1a. This causes origin sensor 120 to close thereby emitting a signal of level L which causes AND gate 175 to emit a signal of level L which in turn causes XOR gate 136 to emit a signal of level H which turns off red LED 134.

Also when delay circuit 200 emits a signal of level H, OR gate 226 emits a signal of level H which, in turn, activates breaker 111 thereby disconnecting battery 92 from control circuit 109.

(v) Terminating an Operation by Releasing the Trigger

Should the operator release trigger 86 thereby opening operation control switch 117, before adjustable counter 180 reaches the programmable number, a fail-safe termination of the operation will occur in the following sequence.

Opening operation switch 117 causes the signal in line 233 to assume a signal of level H. Since the Q output of flip-flop 170 is also at a signal of level H during an operation, AND gate 201 is satisfied and produces a signal of level H. Since adjustable counter 180 has not yet reached the programmable number, adjustable counter 180 produces a signal of level L on line 241 which is inverted and applied to AND gate 206 along with the output of AND gate 201, causing the output of AND gate 206 to produce a signal of level H. This satisfies OR gate 220 which produces on line 238 a signal of level H, which is applied to OR gate 185 which, in turn, activates motor counter-clockwise control circuit 154 to turn plunger carriage motor 55 counter-clockwise which, by means of plunger carriage motor gear box 56, turns plunger lead screw 50 in a counter-clockwise direction which moves plunger support bracket 45 forward pushing plunger 5 forward into the syringe body 4, and pushing stylet 3 forward to occlude needle 2.

A signal of level H on line 238 also blocks control signals from being applied to motor clockwise control circuit 153 with AND gate 188, and blocks control signals from being applied to solenoid control circuits 160 and 161 with AND gates 199 and 197.

Simultaneous with the opening of operation control switch 117, main control cut off switch 118 and detent solenoid cut off switch 119 also open, thereby deenergizing main solenoid 70 and detent solenoid 66. The deenergization of main solenoid 70 and detent solenoid 66 allows syringe carriage 40 to move rearward through action of syringe carriage helical return springs 61, along with the entire carriage assembly, to the origin position shown in FIG. 1a.

If there are no operational erros, origin sensor 120 will close, thereby producing a signal of level L on line 235 when syringe carriage 40 returns to the original starting position as shown in FIG. 1a. The signal of level L produced by origin sensor 120 is inverted and applied to AND gate 202 along with the signal of level H produced by AND gate 201. This causes AND gate 202 to produce a signal of level H which is delayed by delay circuit 203 and applied to OR gate 226. This causes the output of OR gate 226 to produce a signal of level H on line 232 which, in turn, causes breaker 111 to open power switch 110, thereby removing power from control circuit 109.

If, however, an error does occur and syringe carriage 40 does not return to the original starting position (for example, if an electromechanical failure or jam has occurred), origin sensor 120 will not open before delay circuit 207, which delays the output of AND gate 206 and produces a signal of level H. The signal of level H produced by origin sensor 120 on line 235 is applied with the signal of level H produced by delay circuit 207 to AND gate 208 which, in turn, satisfies three-input OR gate 223, which produces a signal of level H. The output signal of level H produced by OR gate 223 is applied to buzzer control circuit 138 which activates buzzer 137 warning the operator that needle tip 19 is exposed. In addition, a signal of level H produced by OR gate 223 is applied to OR gate 224, and, after a delay determined by delay circuit 225, line 231 also carries a signal level of H thereby breaking fault indicating breaker 228 and, through OR gate 226 and line 232, breaking circuit breaker 111 and opening power switch 110.

(vi) Failsafe Shutdown of Operation Due to an Electromechanical Fault

The fine needle aspiration apparatus of the present invention also provides for failsafe shutdown should an error such as a mechanical jam or an electromechanical failure occur. This is accomplished by providing delay circuits which time various occurrences under normal operation. Should these occurrences take longer than necessary, possibly indicating a fault, respective delays will expire initiating an organized and safe shutdown of the device.

Specifically, the operation of main solenoid 70 and detent solenoid 66 is monitored by a circuit including delay circuit 211 and AND gate 212. If the Q output of flip-flop 195 on line 243 has a signal level of H, indicating that main solenoid 70 should be energized through AND gates 198 and 199 and through main solenoid control circuit 160, and if origin sensor 120 remains closed producing a signal of level L on line 235, and if this condition exists for a time determined by delay circuit 211, this indicates that syringe carriage 40 has failed to move from the origin position, despite a command to do so, and is reflected by a signal level of H at the output of AND gate 212.

Also, if the Q output of flip-flop 195 changes from H to L, and if origin sensor 120 closes before expiration of the delay of circuit 211, indicating that syringe carriage 40 has not stopped at detent 65, AND gate 212 will produce a signal of level H.

Similarly, if after a time determined by delay circuit 213, the front drive bar sensor 125 is not closed indicating the incomplete forward movement of syringe carriage 40, as commanded by a signal of level H on the Q output of flip-flop 195 on line 243, AND gate 214 will produce a signal of level H.

The forward and rearward motion of plunger support bracket 45 are monitored by delay circuits 215 and 217 and AND gates 216 and 218. Specifically, if, after a time delay determined by delay circuit 215, front plunger limit sensor 127 is not closed, thereby producing a signal of level L on line 236, despite a command to move the plunger support bracket forward emitted by AND gate 184 on line 237, AND gate 216 will produce a signal of level H. Similarly, if after a time determined by delay circuit 217, rear plunger limit sensor 128 has not closed, thereby producing a signal of level L on line 244, indicating that plunger support bracket 45 has not moved completely forward despite a command to do so emitted by AND gate 188, AND gate 218 will produce a signal of level H.

OR gate 219 accepts the outputs of each of AND gates 212, 214, 216 and 218. Should any of these AND gates produce a signal of level H, OR gate 219 will produce a signal level of H. This immediately deactivates the device by producing a signal of level H on line 238 through OR gate 220 (thereby deactivating detent solenoid 66, main solenoid 70 and commanding motor 55 to turn counter-clockwise thereby returning plunger 5 back into syringe body 4, as described above). In addition, a signal of level H output by OR gate 219 will, through OR gate 224 and delay circuit 225, activate fault indicating breaker 228 via line 231 and, through OR gate 226, activate breaker 111 through line 232. In addition, if the output of OR gate 219 remains at a signal of level H for a time period determined by delay circuit 221 without origin sensor 120 closing, thereby indicating that plunger support bracket 45 has not returned to the origin position shown in FIG. 1a, AND gate 222 will produce a signal of level H which, via OR gate 223, will activate buzzer 137 through buzzer control circuit 138, thereby notifying the operator that needle tip 19 is exposed.

The function of fault indicating breaker 228, once it has been tripped open by delay circuit 225, is to prevent any use of the apparatus, by disconnecting the power from battery 92 to electronic control circuit 109. Once fault indicating breaker 228 has been tripped, the electromechanical or jam failure must be found and repaired and fault indicating breaker 228 must manually be reset before the apparatus can be used again.

As will be appreciated by those skilled in the art, the present invention is not limited to control by solid-state logic, and could be implemented, in whole or in part, with microprocessor control, wherein any number of the control functions are programmed via software or hardware. Moreover, as will be appreciated, one or more of the automated functions of the apparatus could be eliminated and performed manually by the operator.

Furthermore, although the above-described embodiment as set forth herein is electrically operated, it may be desirable to substitute certain pneumatic components for the electro-mechanical components described herein. In this regard, the main solenoid 70 could be substituted with a pneumatic piston with appropriate valving and a pneumatic gas source, e.g., carbon dioxide.

In lieu of the manual method above described for expressing the collected sample onto the microscope slide (i.e., detaching the needle and attaching an air-filled syringe to express the sample), the first embodiment of the invention can be modified to include an automatic feature, as discussed below. In the modified first embodiment incorporating an automatic expression feature, an orifice is provided in the rear portion of cylindrical syringe body 4. Additionally, rear plunger limit sensor 128 is relocated so as to be activated before the plunger 5 has been fully extended rearward into contact with the end plate 59. A further sensor (the plunger expression sensor) is also provided to sense the rearwardmost excursion of the plunger 5, i.e., that position where the plunger contacts the end plate 59. Sensor 128 is located such that when the plunger support bracket activates the sensor, the orifice in the syringe body does not communicate with the syringe chamber 34. However, when the plunger moves to its rearwardmost excursion and contacts the plunger expression sensor, the orifice communicates the chamber 34 of the syringe with the atmosphere.

Operation of the apparatus during the aspiration cycle is in all respects similar to the operation described above, except that, during the aspiration cycle, the plunger is only withdrawn until contact is made with relocated sensor 128. That is, the plunger does not withdraw into contact with end plate 59. However, after completion of the aspiration cycle, a further automatic sample expression cycle is initiated with the modified embodiment of the present invention.

The automatic expression cycle operates as follows. After the operator has removed the needle and sheath from the patient, and positioned the needle-tip above a slide upon which the sample is to be expressed, a sample expression switch located away from the trigger is activated by the operator. Upon activation of the sample expression switch, the plunger 5 is withdrawn once again, but in this cycle, the plunger continues to withdraw until it contacts the plunger expression sensor at end plate 59. This rearward movement of the plunger opens the orifice in the side of the syringe body to the syringe chamber 34, thus allowing air to fill the barrel of the syringe. After the syringe is filled with air, the motor winds the plunger in slowly, once again blocking the orifice in the side of the syringe, thus trapping air in the syringe chamber. The collected sample is then expressed onto the microscope slide as the motor continues to slowly move the plunger forward. Release of the trigger at any time during the expression cycle causes the motor to stop. Depression of the trigger again allows the motor to once again advance, causing further sample to be expressed. After the plunger is in its forwardmost position, the motor shuts down and the expression cycle is completed.

Additional modifications to the expression cycle can be made to further facilitate automatic sample expression. The expression cycle can be modified such that the motor moves slowly only during a first phase of the forward movement of the plunger, and thereafter speeds up to quickly return the plunger to its forwardmost position. In this manner, the complete duration of the expression cycle is reduced such that the motor only moves slowly while the sample is actually being expressed from the needle to the slide.

Thus, with minor modifications in the control circuit and sensors of the present invention and in the syringe design, an automatic expression feature can be incorporated in the first embodiment.

As noted in the above discussion of the first preferred embodiment, at the completion of each fine needle aspiration procedure, the needle 2, stylet 3, syringe 4 and plunger 5 must be replaced. However, the first embodiment can be modified to employ a reusable syringe and plunger. When a reusable syringe and plunger are employed, it is no longer necessary to allow operator access to a substantial portion of the upper part of the apparatus. Accordingly, the apparatus can be substantially sealed from outside contamination with access being provided only to the extent necessary to replace the needle and stylet. Secondly, by providing a reuseable syringe and plunger, the operational costs associated with the use of the apparatus can be reduced since it is necessary to replace only the needle and stylet after each procedure. However, the provision of a reuseable syringe and plunger is somewhat problematic since the stylet must be operatively connected to the plunger in the first embodiment.

The aforementioned difficulties can be obviated through the use of an automatic stylet grabber assembly, discussed hereinafter with reference to FIGS. 19a, 19b, 20a and 20b.

FIGS. 19a–19b illustrate a first preferred stylet grabber which is electrically actuated. The grabber includes a pair of grabber pawls 308, 309 which are respectively pivotably mounted on a pair of bearing pins 312, 313. The forward end of the grabber pawls 308, 309 include grabber jaws 310, 311. A compression spring 315 is located between the pivot points defined by the bearing pins 312, 313 and the grabber jaws 310, 311 so as to bias the grabber jaws apart as shown in FIG. 19b. The stylet grabber also includes a cam 318 defined at the end of a solenoid plunger 305 of a solenoid 320. A tension spring 322 biases the plunger 305 away from the grabber pawls 308, 309. As shown in FIGS. 19a and 19b, the stylet grabber is located in a central portion of plunger head 307. As in the previous embodiments, the plunger head includes plunger seals 306 which maintain airtight contact between the outer periphery of the plunger head 307 and the inner periphery of the syringe body 304.

As shown in FIG. 19a, when the solenoid 320 is energized the solenoid plunger 305 is driven forward against the bias of tension spring 322. Forward movement of plunger 305 causes cam 318 to engage pawls 308, 309, thereby forcing the pawls to pivot about the bearing pins 312, 313 so as to compress spring 315 and close the jaws 310, 311 around the head of stylet 303.

However, as shown in FIG. 19b, when the solenoid 320 is deenergized, the solenoid plunger 305 is retracted by the tension spring 322, allowing the grabber pawls 308, 309 to open under the force of compression spring 315.

Those skilled in the art will recognize that the electrically actuated stylet grabber disclosed herein is easily adaptable for use in the automatic fine needle aspiration embodiment discussed above by substituting the modified plunger shown in FIGS. 19a and 19b for the conventional plunger 5 employed in the previously described embodiment. A conventional syringe can be, but need not be, employed. Any syringe and plunger which cooperate to create the requisite suction upon withdrawal of the plunger are sufficient for operation of the apparatus. Moreover, casing 1 should be modified such that cover 82 only provides access to the front portion of the apparatus. The rear portion of the casing is sealed to avoid contamination.

The needle and stylet should preferably include a filter 22 extending between the interior surface of the needle and the exterior periphery of the stylet as discussed above in connection with FIG. 12 to prevent contamination of the interior of the syringe and plunger. The filter should be located proximate the rear end of the needle (near the luer-lock connection) to minimize any reduction in volume of the cell sample storage portion of the needle caused by the the filter.

Having thus described the structure of the electrically actuated stylet grabber as well as the applicability of the stylet grabber to the fine needle aspiration apparatus described above, description will now be made of the operation of a fine needle aspiration apparatus incorporating an electrically actuated stylet grabber of the type discussed above.

First, the operator opens the cover of the aspiration apparatus, thus turning the cover switch off and disconnecting power to the device, as discussed above. Because the syringe and plunger need not be replaced, it is necessary only to expose the front portion of the syringe (including the luer-lock socket 330) when the cover is opened. The remainder of the syringe and plunger are sealed against contamination.

The operator thereafter attaches a needle to the syringe body via the luer-lock connections. The needle and stylet are configured such that when the needle is attached to the syringe via the luer-lock, the stylet extends into the syringe past the grabber jaws 310, 311 as shown in FIG. 19b.

After the needle is attached to the syringe via the luer-lock (and the stylet is positioned inside the grabber jaws), the cover is closed. A needle sheath is thereafter attached to the outer portion of the apparatus via a second luer-lock connection in the manner described above.

The operator then positions the tips of the needle and stylet as discussed above and depresses the safety switch. Activation of the safety switch energizes the solenoid 320 of the stylet grabber causing the solenoid plunger 305 to move forward from the position shown in FIG. 19b to the position shown in FIG. 19a. As shown in FIG. 19a, movement of the solenoid plunger 305 forward forces the grabber pawls 308, 309 to pivot about the bearings pins 312, 313 such that the grabber jaws 310, 311 are closed around the head of the stylet 303 against the bias of the compression spring 315. Thus, so long as the solenoid 320 is energized, the grabber jaws 310, 311 securely hold the end of stylet 303.

After turning on the safety switch, the trigger is pulled and the aspiration procedure proceeds as described above.

After the red warning LED 134 signals completion of the procedure, the power to solenoid 320 is removed, such that solenoid 320 is deenergized and the solenoid plunger 305 returns to the retracted position thus allowing compression spring 315 to bias the grabber jaws 310, 311 to the open position illustrated in FIG. 19b.

The sheath is then disengaged from the outside of the housing, the cover is opened and the needle is disengaged form the syringe and withdrawn along with the stylet. The stylet is then removed from the needle and discarded. A fresh air-filled syringe is then connected to the needle and the sample is expressed onto a slide for analysis as described above. Alternatively, if the automatic expression feature is incorporated in the apparatus, the sample is automatically expressed as described above, before the needle is removed.

Although the stylet grabber described above is electrically actuated, a manual stylet grabber can also be implemented. In particular, manual means can be incorporated within the apparatus to engage jaws 308, 309 with the head of the stylet. Moreover, any conventional jaw or chuck could be incorporated for this purpose. Preferably, appropriate sensors preclude operation of the apparatus if the jaws are not first properly engaged with the stylet.

Figure 20A:
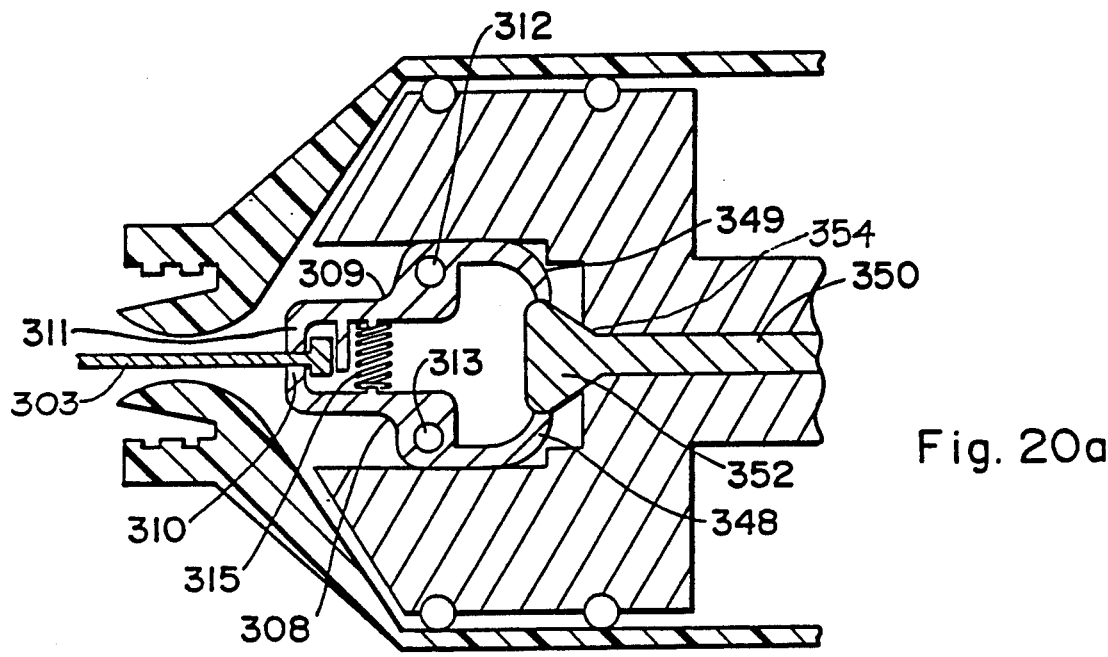
FIGS. 20a and 20b are cross-sectional views illustrating still further modifications of the first embodiment of the present invention.
Figure 20B:
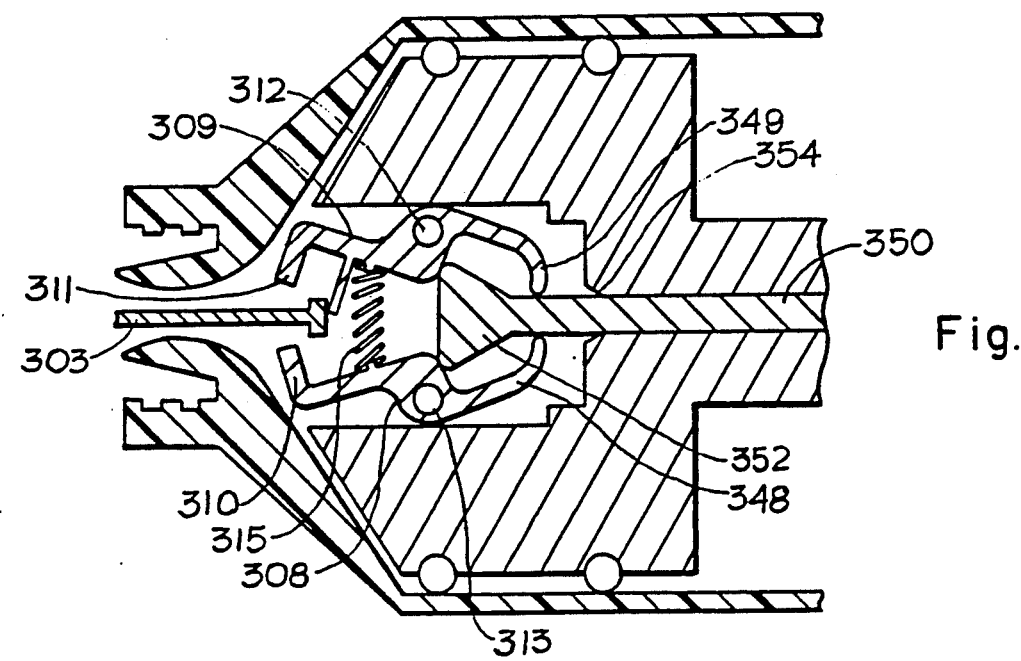

FIGS. 20a and 20b illustrate an automatic mechanical stylet grabber assembly. The mechanical stylet grabber is similar in many respects to the electrically actuated stylet grabber described above. In particular, like the electrical stylet grabber, the mechanical stylet grabber is adapted to be arranged within the plunger head and for use with a needle of the type described above. Further, the grabber itself includes a pair of grabber pawls 308, 309, a pair of bearing pins 312, 313, a compression spring 315, and a pair of grabber jaws 310, 311 which are similar to those of the electrically actuated stylet grabber.

However, unlike the electrically actuated grabber embodiment, the grabber pawls of the mechanical stylet grabber are specially shaped to include curved camming projections 348, 349. Additionally, the plunger 5 is modified to include a central cam rod 350 which has an enlarged cam head 352 adapted for engagement with the ends of the camming projections 348, 349.

In an apparatus incorporating the mechanical stylet grabber, it is the cam rod of the plunger 350 which is connected to the plunger support bracket 45 in FIG. 13 for retracting the plunger relative to the syringe. Thus, at the point during the cycle when the plunger is normally withdrawn from the syringe in the first embodiment, the cam rod is withdrawn from the position shown in FIG. 20b to the position shown in FIG. 20a in the modified first embodiment such that the enlarged camming head 352 of the cam rod 350 engages the projections 348 and 349 so as to pivot the grabber pawls 308, 309 against the bias of the compression spring 315 causing grabber jaws 310, 311 to close about the head of the stylet 303. As the cam rod is further withdrawn, a portion of the enlarged cam head is received within a recess 354 in the plunger such that the continued retraction of the cam rod 350 causes the entire plunger 5 to retract, as required for the aspiration procedure.

While the mechanical stylet grabber described above includes a compression spring 315 to normally bias the grabber pawls 308, 309 into the open position, in FIG.

20b the opening of the pawls could be accomplished without a compression spring by configuring the enlarged camming head 352 and the grabber pawls 308, 309 such that when the enlarged camming head is in the extended position shown in FIG. 20b, the enlarged camming head cams the grabber pawls 308, 309 into the open position without the aid of a compression spring.

Those skilled in the art will appreciate that like the electrically actuated stylet grabber, the mechanical stylet grabber described above is adapted for use in fine needle aspiration apparatus of the type previously described herein with only minor modifications in the syringe, plunger, needle, stylet and casing.

Having thus described the mechanical stylet grabber and its applicability to fine needle aspiration apparatus of the type described above, a description will be made herein of the operation of a fine needle aspiration apparatus which includes the mechanical stylet grabber discussed above.

As with the electrically actuated stylet grabber, the operator begins by opening the cover thereby turning off the cover switch and disconnecting all power to the apparatus. The operator then inserts the stylet into the syringe while attaching the needle to the syringe via the luer-lock. The operator then closes the cover such that the cover switch is actuated and attaches the sheath to the apparatus housing via a second luer-lock.

After manually positioning the tips of the needle and stylet, the operator turns on the safety switch and pulls the trigger thus initiating the aspiration cycle. The cycle is carried out as described above except that central cam rod 350 (and not plunger 5) is connected to and directly retracted by the plunger support bracket 45. Withdrawal of central cam rod 350 causes the plunger to be withdrawn from the syringe while also causing the stylet grabber to grab the head of the stylet 303 as shown in FIG. 20a. After the procedure is performed, the plunger is returned to its forward position and the cam rod 350 is moved to its full forward position, causing the grabber jaws 310, 311 to return to the open position shown in FIG. 20b.

Upon completion of the procedure, the operator disengages the sheath from the housing and opens the cover. The needle and stylet are then disengaged from the syringe and the stylet is removed from the needle and discarded. The sample is then expressed manually as described above. Alternatively, if the above-described automatic expression feature is included in the apparatus, the automatic expression cycle is performed before the needle and sheath are removed.

In certain applications it is desirable to conduct a test run of the automatic fine needle aspiration apparatus before conducting an actual biopsy on the patient. Additionally, in certain cytological analyses it is preferred to draw the cytological sample into a saline suspension to facilitate expression of the collected sample.

With reference to FIGS. 13–16, it is apparent that certain problems could be encountered in attempting to conduct a test run when the needle is not embedded within a target area. Specifically, if the aspiration cycle is so performed, rather than creating a partial vacuum upon withdrawal of the plunger 5 from the syringe 4, air is drawn into the syringe air chamber 34 as the plunger is withdrawn. Upon conclusion of the test cycle, such air is trapped in the syringe air chamber 34 when the stylet tip 26 seals the narrow diameter portion 16 of needle 2. This trapped air could have a tendency to stall or place an undue burden upon plunger carriage motor 55, possibly preventing the return of the plunger to its origin position.

Figure 21:
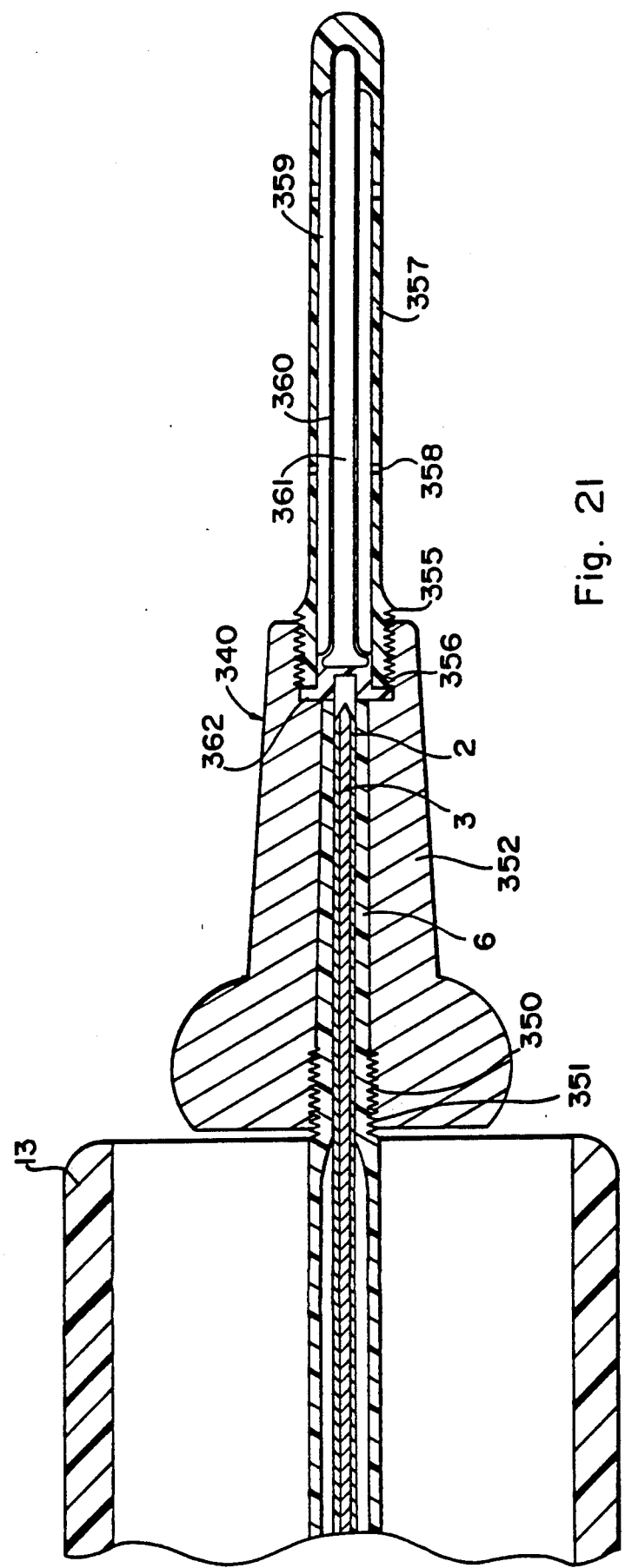
FIG. 21 is a cross-sectional view of a resevoir test apparatus for use with the first embodiment of the present invention.

Accordingly, to avoid drawing air into the syringe chamber 34 during a test run, or to otherwise introduce saline into the cell sample storage portion 20 of the needle 2, the sheath 6 can be modified to accommodate a test reservoir apparatus as illustrated in FIG. 21. The sheath 6, stylet 3, needle 2 and sheath finger guide 13 are identical to the embodiment of FIGS. 2–8 except that sheath 6 is modified to define external threads 350 to removably receive internal threads 351 of hub 352 or some other appropriate attachment means of a test reservoir apparatus 340.

A reservoir support housing 357 is threaded via threads 355, 356 to hub 352 and defines an interior chamber 359. A pouch 360 is located within chamber 359 and has flanged end 362 captured between shoulders defined by hub 352 and reservoir support housing 357. Pouch 360 is made from a soft, puncturable, resilient material, such as silicone or surgical rubber and is filled with a small volume of air, saline, or a combination thereof 361. Chamber 359 and pouch 360 are dimensioned such that a small space remains between the interior wall of chamber 359 and the outer surface of the pouch. Vent holes 358 are defined along the wall of chamber 359.

Having described the structure of the test reservoir apparatus, its operation is hereinafter described. Should the operator determine that a test run of the apparatus should be performed or that saline should be drawn into the cell sample storage portion of the needle before performing a biopsy on the patient, a modified sheath having a test reservoir apparatus 340 threaded thereto should be selected.

To initiate the test run, the operator installs the modified syringe and sheath in accordance with the procedure described above with respect to the first preferred embodiment of the invention, including installing the syringe 4, closing the cover 82 and mounting the sheath 6 via luer-lock connections 11, 81.

The operator thereafter initiates a test run by performing the safety/trigger sequence discussed above. Depression of the trigger causes needle 2 to advance forward, piercing pouch 360 and aspirating the contents 361 of the pouch (i.e., the saline, air or mixture thereof). The pouch is air tight, so that the amount of air or fluid drawn into the syringe is limited to the volume of the pouch. Because the pouch has a small volume (e.g., 25–50 λ), an insufficient amount of gas or fluid is drawn into the syringe to have any adverse affect upon motor performance or upon return of the plunger to its origin position.

Upon completion of the test aspiration cycle, most of the contents of pouch 360 remain within the cell sample collection portion 20 of the needle 2. Accordingly, if it is desired to suspend the biopsy sample in saline, pouch 360 should be filled with saline for the test run. After completion of the test run, the test reservoir apparatus 340 is unthreaded from sheath 6 at threads 350, 351, discarded, and the apparatus is tested and ready for biopsy on the patient.

As will be apparent to those ordinarily skilled in the art, the test run apparatus of FIG. 21 thus performs a dual function of enabling a test run and introducing saline to the cell sample storage portion of the needle.

Although the description thus far has been directed to an automatic apparatus for performing fine needle aspiration, it will be appreciated by those skilled in the art that one or more of the operations of the automatic apparatus can be performed manually, thus simplifying and reducing the cost of the overall apparatus.

To this end, FIGS. 22-23 illustrate a second embodiment, which is manually operable, but which provides many of the beneficial features of the present invention. The manual embodiment of FIG. 22 includes a variable gage needle 402, configured as in FIGS. 2-8 or 9. A sheath 406 surrounds the needle in the manner described above with respect to the automatic embodiment, and can also be one of various configurations, as described with reference to FIGS. 2-8, 10 and 11. In lieu of the sheath luer-lock connection 11 in FIG. 13, sheath 406 in the first manual embodiment has an outwardly tapering mouth 411 to facilitate insertion of the needle assembly therein. Stylet 403 is located within needle 402 and, when in its forwardmost position, occludes the narrow diameter portion of needle 402 (not shown in FIG. 22). Needle 402 is connected to syringe body 404 via luer-lock connections 418, 431 on the needle and syringe body, respectively. Syringe plunger 405 is located within syringe body 404 and defines, with the syringe body, a syringe air chamber 434. Stylet 403 extends through plunger 405 and is movable therewith. Stylet 403 has stylet head 427 which is press fit into the end of plunger 405, or otherwise removably retained therein in any expedient manner.

Stop 423 is slidable along needle 402, and is securable to the needle via thumbscrew 422 or in some other expedient manner. A gage 424 is printed or inscribed on needle 402, and may include color-coded segments to facilitate operator-observation of the extent of penetration and the reciprocation excursion range, in a manner hereinafter described in more detail.

Syringe handle portion 426 is integral with or connected to syringe body 404. Plunger handle portion 428 is integral with or connected to plunger 405, and is slidable along rails 430 of the syringe handle portion in the axial direction. Holes 429 and 432 are provided in syringe handle portion 426 and plunger handle portion 428, respectively, to permit insertion and withdrawal of the stylet.

The entire unit illustrated in FIG. 22 may be configured as a sterilized disposal unit, in which case, the syringe handle portion and plunger handle portions are made from a low-cost, light-weight plastic. Alternatively, the handle portions can be reusable, made from, e.g., stainless steel, and the syringe, plunger, needle, stylet and sheath can be disposable and removably insertable into the handle portions.

Rails 430 of syringe handle portion 426 can be configured with helical spring means (similar to springs 61 in FIG. 16), to bias the handle portions to the position illustrated in FIG. 22.

FIG. 23 illustrates a modification of the embodiment disclosed in FIG. 22, which includes a cell expression valve, indicated generally as 520. In the FIG. 23 embodiment, needle 502 is substantially the same as needle 402, except that it includes orifice 509 and valve hub 507 at its end remote from the needle tip. Valve hub 507 locates rotary gate valve 510. Rotary gate valve 510 has orifice 508 adapted to communicate with orifice 509 of the needle when in the open position illustrated in FIG. 23. The needle, with the valve assembly, is connected to the syringe assembly as in FIG. 22, via luer-lock connections 518, 531. Gate valve 510 is rotatable about needle 502 between valve hub 507 and luer-lock connection 518 to block orifice 509 when in its closed position.

Having described the structural aspects of the embodiments of FIGS. 22-23, the operation thereof is hereinafter described with reference to the figures.

Similar to the discussion above with respect to dials 71, 72 in connection with FIG. 13, the operator first determines the desired depth of penetration and range of excursion based upon the size and location of the target area being biopsied. After the maximum penetration depth has been determined, the operator sets the excursion stop 423 via thumbscrew 422, thereby limiting the forwardmost movement of the needle with respect to the sheath. The operator also determines the appropriate color-coded or otherwise designated portion of the gage 424 corresponding to the desired reciprocation limit. Having undertaken these preliminary set-up steps, the operator is now ready to commence the biopsy procedure.

First, the sheath and related assembly are positioned next to the target area in the manner described above with respect to the first embodiment. The operator should carefully observe gage 424 while inserting sheath 406 to ensure that the needle does not emerge from the sheath while the sheath is being positioned. If an ultrasonic transducer is being used, the operator probes until the target area and needle entry point are determined. If the target area is the prostate and ultrasound is not utilized, the apparatus is inserted trans-rectally and the operator palpates the prostate to determine the target area and needle entry point.

Thereafter, the operator pushes the needle forward by pushing forward on the handle assembly, causing the needle to protrude from the sheath 406 and pierce the target area. Forward movement of the needle is limited by the abutment of stop 423 with end 411 of sheath 406.

The operator then squeezes together the plunger handle portion 428 and syringe handle portion 426, thereby causing withdrawal of the stylet. Such withdrawal unoccludes the narrow diameter portion of the needle and creates a vacuum at the needle tip. The full excursion of the plunger handle portion 428 is determined to correspond to the extent of the desired plunger and stylet withdrawal. If the handle portions are reusable, variable limits (e.g., movable stops or pins in the syringe handle portion 426 which engage the plunger handle portion 428) can be incorporated in the handle portion to render the plunger excursion variable. When the handle portions are fully squeezed together, the tip of the stylet is in the large diameter portion of the needle, as discussed above. If the optional springs are incorporated in the handle portions, as discussed above, continuous pressure is required to maintain plunger withdrawal and keep the stylet from occluding the needle. Accordingly, should the operator be required to immediately withdraw the needle, e.g., if the patient begins to move, the operator need only release the plunger handle portion so that it will return to its initial position, causing the stylet to move forward, occluding the narrow portion of the needle. This return of the plunger and stylet ensures that the stylet is returned to its initial position to avoid contamination of the sample, e.g., with rectal mucosa or bacteria, upon withdrawal of the needle.

After the plunger has been withdrawn, the procedure is continued by reciprocating the handle assembly so that the needle reciprocates with respect to the sheath. Forward reciprocation is limited by the engagement of stop 423 with sheath end 411. The operator controls return reciprocation precisely and conveniently by observing the color-coded or otherwise indicated gage 424, thereby ensuring that the needle is not withdrawn too far, e.g., back into the sheath.

As discussed above, reciprocation of the assembly causes cytological sample to be collected in the sample storage portion of the needle. After sufficient sample is collected, the operator squeezes the syringe and plunger handle portions together to the closed position or, if the optional springs are included on handle rods 430, simply releases the plunger handle portion. Forward movement of the plunger and stylet releases the vacuum and causes the stylet to occlude the needle, protecting the sample from contamination during withdrawal, as discussed above.

The operator then expresses the sample onto a microscope slide in one of several methods, depending on the particular embodiment of the device which is employed.

In the embodiment disclosed in FIG. 22, the stylet 403 can be removed by grasping stylet end 427 and pulling it through holes 429, 432. The needle hub is then disconnected from the syringe luer-lock 431. Thereafter the handle portions are pulled together causing the syringe air chamber 434 to fill with air. The luer-lock connection is then reestablished and the operator depresses the plunger with the needle tip adjacent to a microscope slide. Depressing the plunger causes the sample to be expressed from the sample storage portion to the slide. Although not discussed above in connection with FIG. 13, it will be appreciated by those skilled in the art that this method of sample expression can also be utilized in connection with the automatic embodiment of FIG. 13, discussed above. Also, in lieu of removal of the stylet, the syringe body can include an orifice for communicating the air chamber with the atmosphere, as discussed in more detail below.

Alternatively, the needle can be disconnected and attached to an air-filled syringe for sample expression, as discussed in connection with the first embodiment.

In the embodiment illustrated in FIG. 23, expression of the sample is facilitated by the provision of valve 520. To express the sample in this embodiment, the operator opens valve 520 by rotating gate 510 until orifices 508 and 509 are in communication. The operator then withdraws the plunger as described above, drawing air into the syringe air chamber. The operator then closes valve 520, blocking communication of the orifices and removes the stylet. The sample is now ready for expression in the manner described above. Although not incorporated in FIG. 13, it will be appreciated that the FIG. 13 embodiment could be modified to incorporate a valve identical to valve 520 to facilitate sample expression in the FIG. 13 embodiment.

Many of the advantages associated with the automatic embodiment are achievable with the present manual embodiment. First, the biopsy can be performed by a single operator without requiring cumbersome manipulations. Moreover, a stylet is used to occlude the needle both during insertion and withdrawal of the needle, thus avoiding the contamination of the target area and the sample. Furthermore, stop 423 and gauge 424 provide simple means for standardizing the procedure and monitoring the needle excursion. Finally, all contaminatable portions of the apparatus are disposable and are inexpensive to manufacture.

A third embodiment of the present invention, which is manually operable, is illustrated in FIGS. 24a-24c.

FIGS. 24a-24c illustrate a further needle and sheath assembly for collecting biopsy samples from an internal organ for cytological analysis in accordance with the fine needle aspiration technique. The apparatus is adapted to retrieve a cytological sample of sufficient volume (e.g., approximately 25-50 $\lambda$ of cells and intracellular fluid from tissue) without retrieving a core. Moreover, the apparatus facilitates retrieval of the sample only from the target area, without collecting undesired debris or contaminants. With this apparatus, biopsies can be performed by a single person, and standardization of the fine needle aspiration technique is achievable.

The embodiment illustrated in FIGS. 24a-24c consists of a needle 610 (e.g., 21-24 gauge) with a closed or bullet tip 611 and a series of side ports 612 positioned just behind the tip opening. To facilitate sample expression, the side ports should be located substantially in the same radial direction or only slightly offset. This will ensure that the sample, when expressed, can be directed onto a microscope slide. A sleeve 620 (e.g., 22-19 gauge) is closely fitted around needle 610 such that a seal of the side ports 612 is effected when the sleeve 620 is in its forwardmost position (as illustrated in FIGS. 24a and 24b). In addition, to improve the seal between needle 610 and sleeve 620 and to reduce the required manufacturing precision, one or both of the needle and sleeve can be coated with plastic or silicone or other suitable material, to act as a gasket or seal between the needle and sleeve. The rear end of the sleeve 620 has annular ring 621 and outer retaining tube 622 secured thereto. The outer retaining tube locates an inner retaining tube 631 permanently fixed to a needle hub 630 fixed to needle 610. A compression spring 626 surrounds the needle 610 and is interposed between annular ring 621 and needle hub 630. Spring 626 is surrounded by outer retaining tube 622 and inner retaining tube 631.

A sheath 640 surrounds sleeve 620 and outer retaining tube 622 and is provided at its end adjacent to the needle tip with a tip or handling apparatus 641 appropriate for the particular region of the body being biopsied. The exemplary tip 641 in FIG. 24 is effective, e.g., for biopsy of any soft organ to which access can be gained through the skin, e.g., the breast.

The hub 630 of the needle can be provided with a valve 635 which has a port 636 which is alignable with a port 613 in the needle. Alignment of the needle and valve ports opens the valve, allowing air to be drawn into the syringe 650. The needle hub 630 is provided with a luer-lock connection 632 which mates with a syringe luer-lock connection 651. A conventional syringe can be used and fitted to the needle and sheath arrangement, for use with conventional fine needle aspiration handle mechanisms or, for example, a handle as illustrated in FIG. 22. Alternatively, the syringe, needle, sleeve, sheath and handle can be integrally configured as a disposable unit.

A filter 653 is provided in hub 630, and performs the functions discussed above in connection with FIG. 12.

Turning to the operation of the above-described apparatus, the initial position of the apparatus is illustrated in FIG. 24a, with the sleeve 620 and needle tip 611 in the fully retracted position within sheath tip 641. The operator thereafter pushes the syringe forward with respect to the sheath, causing the needle 610 and sleeve 620 to move outward from the sheath as a unit and penetrate the target area of the tissue to be sampled as illustrated in FIG. 24b. As is apparent from FIG. 24b, the ports 612 of needle 610 are occluded by the sleeve 620 while the needle penetrates the tissue into the target region. During this penetration stage, the needle and sleeve are moved forward until annular ring 621 of the sleeve 620 abuts a shoulder of the sheath 640 as illustrated in FIG. 24b. Spring 626 has a spring constant sufficient to enable the needle 610 and sleeve 620 to move forward as a unit and abut the shoulder of the sheath without resultant relative movement between the inner and outer retaining tubes 631, 622.

The operator thereafter pushes the syringe forward further, causing compression of spring 626 which results in a relative movement between outer retaining tube 622 and inner retaining tube 631. As a consequence, needle 610 moves forward with respect to sleeve 620 exposing ports 612. The syringe can be evacuated by withdrawing the plunger (not shown) either before or after the step illustrated in FIG. 24c. After creating a vacuum in the syringe, the needle is reciprocated while unoccluded as illustrated in FIG. 24c for a predetermined number of cycles emperically determined by the desired sample yield. Thereafter, the needle and sheath assembly is withdrawn, thereby returning it to the position illustrated in FIG. 24a. The vacuum can be released at any convenient time before or after the needle has been withdrawn.

Once withdrawn, and after the vacuum has been released, valve 635, similar to valve 520 in FIG. 23, can be opened and air can thereafter be drawn into the syringe. Alternatively, the valve 635 can be opened to release the vacuum. The valve 635 is then closed, and the cell sample is expressed onto a microscope slide by holding the sheath, pushing the needle out so that the ports are exposed and pushing the syringe plunger closed, or allowing it to close if springs are embodied in the syringe handle.

In lieu of the above-discussed methods of expression, the embodiments of FIGS. 22 and 24a-24c can be modified to incorporate alternative expression apparatus. In particular, the syringe bodies of each of these embodiments can be modified to include an orifice at the rearward end of the cylindrical syringe body. Additionally, the handle mechanisms in each of these embodiments can be modified to facilitate two plunger withdrawal limits, i.e., a sample collection limit and a sample expression limit. Any suitable stop for the handle can be utilized to establish the limits, including an adjustable stop mechanism or a removable pin, to vary the rearwardmost movement of the plunger handle portion with respect to the syringe handle portion. During the sample collection cycle, the plunger is withdrawn to the sample collection stop, in which position the orifice in the syringe body does not communicate with the syringe chamber. However, during the sample expression cycle, the plunger handle portion is withdrawn beyond the sample collection limit to the sample expression limit, thus allowing air communication through the orifice in the syringe body to the syringe chamber. The plunger is then returned to the forwardmost position, thereby compressing the air and expressing the sample through the needle tip onto a microscope slide for further analysis. The outer sleeve must be retracted during expression by this method with the third embodiment (FIGS. 24a-24c).

Although the third embodiment has been disclosed in terms of manual operation, it will be appreciated that the apparatus is easily adapted to automation of one or more of the steps of the process, including reciprocation, needle advancement, needle withdrawal and cell expression.

Figure 25:
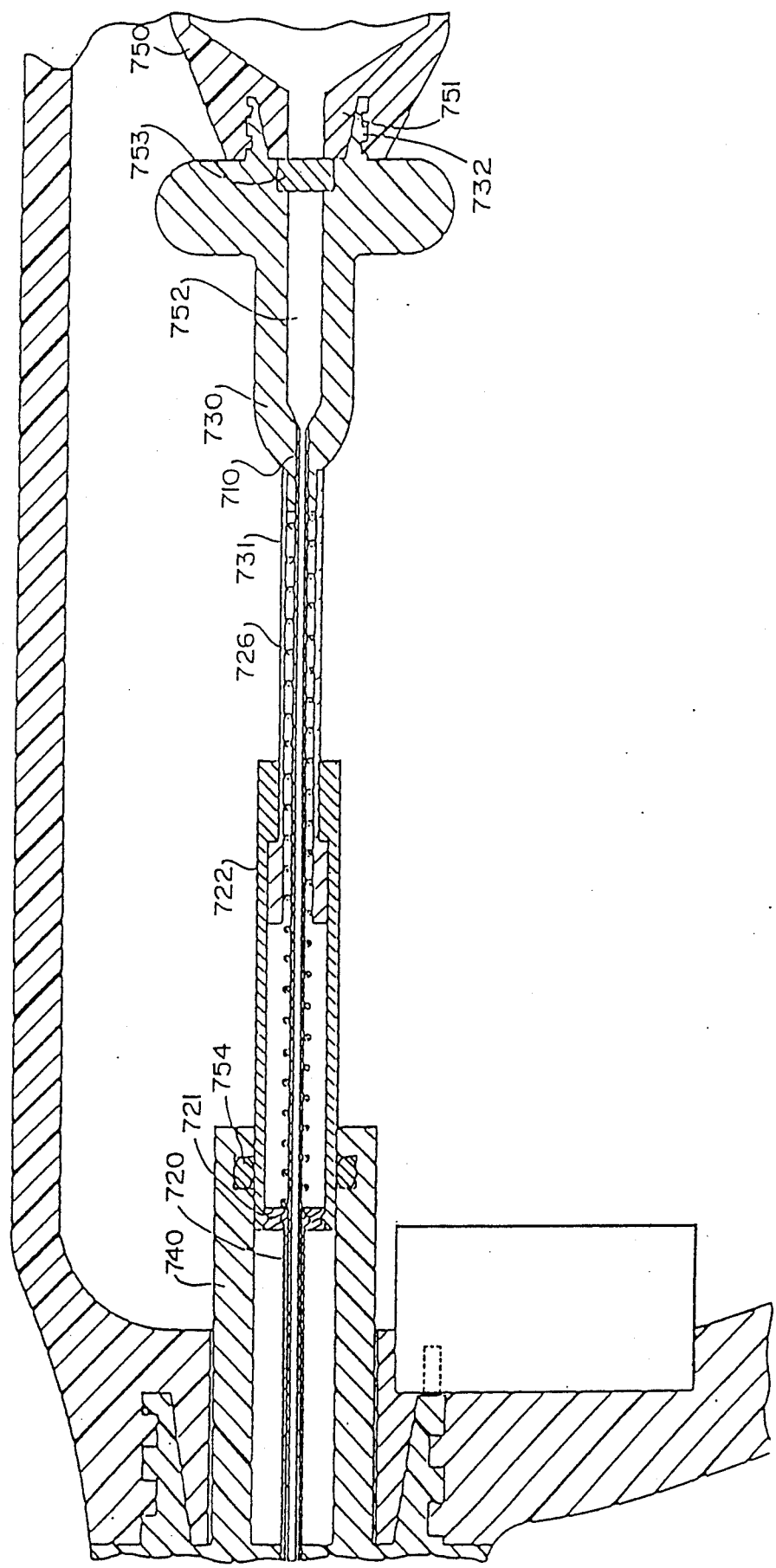
FIG. 25 is a cross-sectional view of an automatic fourth embodiment of the present invention.

FIG. 25 illustrates a fourth embodiment of the invention which illustrates modifications to the first (FIG. 13) embodiment to adapt it for use with a needle and sheath assembly as disclosed in FIG. 24a-24c. FIG. 25 depicts the left-hand portion of FIG. 13, noting modifications thereto. In FIG. 25, similar components to FIGS. 24a-24c are designated by the reference numerals in FIGS. 24a-24c, increased by 100. Specifically, the FIG. 25 assembly includes a needle 710, sleeve 720, needle hub 730, filter 753, luer-lock connections 732, 751, syringe 750, outer retaining tube 722, inner retaining tube 731, compression spring 726, annular ring 721 and sheath 740. Retaining tube 722 is held slidably within an extension of sheath 740 by ring gasket 754, which can be rubber or silicone or any other material having suitable properties.

The apparatus disclosed in FIG. 25 is automatically controlled by the control circuit of FIG. 18 to operate identically with the embodiment of FIGS. 24a-24c. The control of the fourth (FIG. 25) embodiment is substantially identical to the control of the first embodiment, as set forth in FIGS. 17-18.

In operation, the operator inserts the syringe and needle assembly, closes the cover and connects the sheath, as discussed in connection with the FIG. 13 embodiment. To initiate the aspiration cycle, the operator depresses the safety and trigger in the sequence discussed above. In the first step of the automatic aspiration cycle, the carriage assembly moves forward (carrying with it the syringe and needle assembly) until the forwardmost excursion of the needle has been reached (i.e., that excursion corresponding to the position illustrated in FIG. 24c and corresponding to position "B" in FIG. 1). Forward excursion of the carriage assembly is limited by contact of the drive bar with stop 69. The initial forward excursion causes the needle to penetrate the target area in the manner discussed above with reference to the first embodiment. Thereafter the carriage assembly moves rearward under the bias of springs 61 until it abuts detent 65 which is actuated as discussed above by detent solenoid 66. The fourth embodiment is configured such that the needle 710 and outer sleeve 720 remain in the position illustrated in FIG. 24c when the carriage contacts detent 65 (corresponding to position "C" in FIG. 1). Vacuum is then created in the syringe chamber by withdrawing the plunger in the manner described above with reference to the first embodiment. Thereafter, under the direction of the control circuit, the carriage assembly reciprocates a predetermined number of times while the needle is open as depicted in FIG. 24c (i.e., between positions corresponding to "B" and "C" in FIG. 1). After the control circuit senses the completion of the predetermined number of reciprocations, the motor is energized counter-clockwise causing the plunger to retract, thus releasing the vacuum. Detent solenoid 66 is thereafter de-energized, allowing detent 65 to withdraw and the carriage assembly to once again return to its origin position.

As will be appreciated from the foregoing, the construction of the needle and outer sleeve assembly ensures that the needle tip is occluded during the penetration and withdrawal stages of the aspiration cycle. Furthermore, the reciprocation of the needle in the aspiration cycle occurs with the needle unoccluded, causing sample to be drawn into the sample collection chamber. As is apparent from the foregoing, the movements which the fourth (FIG. 25) embodiment undergoes are identical to those of the first (FIG. 13) embodiment, thus enabling identical or substantially identical control circuitry to be implemented in the first and fourth embodiments.

As with the first embodiment, an automated cell expression cycle can also be added to the fourth embodiment. Specifically, as in the first embodiment, an orifice can be located in the rear end of the cylindrical syringe body, sensor 128 of FIG. 13 can be relocated, and an additional plunger expression sensor can be added. With these modifications, the automatic sample expression cycle operates as follows.

During the aspiration cycle, the plunger is not withdrawn to end plate 59 in FIG. 13, but is instead moved only to a first limit position corresponding to the relocated plunger rear limit sensor 128. In this first position, the orifice in the syringe body does not communicate with the syringe chamber 34.

However, during the automatic sample expression cycle, the plunger is further withdrawn until the plunger expression sensor is actuated, in which position the orifice communicates with the syringe chamber allowing the chamber to fill with air. As with the automatic expression cycle discussed above with reference to the first embodiment, the plunger is then moved forward slowly, blocking the orifice, which then creates pressure in the syringe chamber 34 and causes the sample to be expressed from the needle onto the slide. As will be appreciated with reference to FIG. 24c, the main solenoid must be actuated during the automatic sample expression cycle to open the needle ports (i.e., to withdraw the sleeve 720 with respect to the needle 710). The expression cycle is designed so that the sample will continue to be expressed so long as the operator maintains pressure on the trigger. The control circuit for the automatic expression feature can be configured such that after the trigger has been released, again depressing the trigger causes the sample to continue to be expressed. Additionally, the control circuit can be configured such that after a predetermined time or movement of the plunger, the motor speeds up to quickly return the plunger to its forwardmost (closed) position. The time at which the motor begins to speed up should be determined to correspond to a time when all or substantially all of the sample has been expressed from the syringe.

It will be appreciated that certain modifications to the aspiration control circuit can also be made to facilitate the automatic expression feature of the invention. In particular, the above-described aspiration cycle of the FIG. 25 embodiment can be modified such that the plunger is not returned to the forwardmost or closed position at the end of the aspiration cycle. This modification is possible in the fourth embodiment since movement of the plunger is not required to occlude the needle at the time of needle retraction. With the plunger still withdrawn to the first limit position at the conclusion of the aspiration cycle, the plunger need only be moved rearward a small distance to open up communication between the orifice and the syringe chamber. Thereafter, upon initiating the sample expression cycle, expression proceeds in the manner discussed above.

As will be appreciated by those ordinarily skilled in the art, the fourth embodiment of FIG. 25 allows for the use of a permanent (non-disposable) syringe and plunger mounted in a sealed portion of the gun. To this end, access through the cover can be limited to only the luer-lock connection of the syringe if a permanent syringe and plunger are used.

Furthermore, although the carriage and the detent 65 are described as controlled by main solenoid 70 and detent solenoid 66, either or both solenoids could be substituted with other appropriate means, including, but not limited to, D.C. servo or stepping motors with appropriate linkages providing the desired reciprocatory movements as discussed in relation to the first embodiment. Also, it may be desirable to substitute certain pneumatic components for the electro-mechanical components described herein. For example, the main solenoid 70 could be substituted with a pneumatic piston with appropriate valving and a pneumatic gas source, e.g., carbon dioxide.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent extended by the broad general meaning of the terms in which the appended claims are expressed.

What is claimed is:

1. An apparatus for aspirating a cytological sample from a target area, comprising:
   a needle having at least one opening;
   occlusion means for blocking said at least one needle opening when the needle is inserted into and withdrawn from the target area;
   a sheath surrounding at least a portion of said needle and cooperating with said occlusion means to selectively unblock said at least one needle opening;
   reciprocation means for reciprocating said needle and said occlusion means relative to said sheath, said reciprocation means including reciprocation control means for controlling the reciprocation excursion of said needle within the target area, said reciprocation control means including penetration control means for limiting the extent of penetration of the needle into the target area, said penetration control means including a first stop limiting the advancement of said occlusion means exteriorly of said sheath and a second stop limiting the advancement of said needle, wherein said second stop is positioned to permit extension of said needle outwardly of said occlusion means with said occlusion means advanced to said first stop; and
   vacuum means connectable to said needle for selectively creating a partial vacuum at said needle opening.

2. The apparatus for aspirating a cytological sample as set forth in claim 1, wherein said needle has only one opening located at its tip.

3. The apparatus for aspirating a cytological sample as set forth in claim 1, wherein said needle has a closed tip and said at least one opening is on the periphery of the needle near its tip.

4. The apparatus for aspirating a cytological sample as set forth in claim 1, wherein said at least one opening is on the periphery of the needle near its tip.

5. The apparatus for aspirating a cytological sample as set forth in claim 4, wherein said at least one opening is chamferred.

6. The apparatus for aspirating a cytological sample as set forth in claim 4, wherein said occlusion means comprises a sleeve surrounding said needle which blocks said at least one opening when in its occluding position.

7. The apparatus for aspirating a cytological sample as set forth in claim 1, wherein said occlusion means comprises a stylet inside said needle which blocks said at least one opening when in its occluding position.

8. The apparatus for aspirating a cytological sample as set forth in claim 7, wherein said stylet passes through but does not fully occupy said sample collection portion.

9. The apparatus for aspirating a cytological sample as set forth in claim 8, wherein said vacuum means is a syringe and syringe plunger, and said stylet is connected to said syringe plunger.

10. The apparatus for aspirating a cytological sample as set forth in claim 9, wherein said stylet occludes said at least one opening when said syringe plunger is in its forwardmost position, and the syringe plunger is in its forwardmost position when the needle is inserted into and withdrawn from the target area.

11. The apparatus for aspirating a cytological sample as set forth in claim 9, further comprising grabber means for detachably connecting said stylet to said syringe plunger.

12. The apparatus for aspirating a cytological sample as set forth in claim 1, wherein said reciprocation control means comprises forward and rearward stops for limiting movement of the needle.

13. The apparatus for aspirating a cytological sample as set forth in claim 1, wherein said reciprocation control means comprises a stop for limiting forward movement of the needle and a visual gage for monitoring rearward movement of the needle.

14. The apparatus for aspirating a cytological sample as set forth in claim 1, further comprising electrical control means for automatically controlling the apparatus.

15. The apparatus for aspirating a cytological sample as set forth in claim 1, further comprising test apparatus means for introducing a limited volume of at least one of air and saline into the sample collection portion, said test apparatus means being detachably mounted to said sheath.

16. The apparatus for aspirating a cytological sample as set forth in claim 1, wherein said needle, sheath, occlusion means and vacuum means are disposable.

17. The apparatus set forth in claim 1, further comprising bias means interposed between said needle and said occlusion means.

18. An apparatus for aspirating a cytological sample from a target area, comprising:
a needle having a closed tip and at least one peripheral opening;
a sheath;
an outer sleeve surrounding said needle, and cooperating with said sheath, to be movable relative to said needle to and from an occluding position in which said at least one peripheral opening of said needle is blocked by said outer sleeve;
reciprocation means for reciprocating said needle and said outer sleeve between a first position wherein said needle and said outer sleeve extend within said sheath and a second position wherein said needle and said outer sleeve extend exteriorly of said sheath, said reciprocation means including reciprocation control means for controlling the reciprocation excursion of said needle within the target area said reciprocation control means being operable to permit reciprocation of said needle in an unoccluded position relative to said outer sleeve with said outer sleeve fully extended relative to said sheath; and
means for creating a partial vacuum in said needle.

19. An apparatus for aspirating a cytological sample from a target area, comprising:
a needle having a closed tip and at least one peripheral opening;
an outer sleeve surrounding said needle, said needle being movable relative to said outer sleeve to and from an occluding position in which said at least one peripheral opening of said needle is blocked by said outer sleeve;
bias means cooperating with said needle and said outer sleeve for biasing said at least one peripheral opening towards said occluding position;
means for creating a partial vacuum in said needle; and
means for moving the needle into and out of the target area while it is in its occluding position, and for reciprocating said needle over a predetermined excursion range within said target area while it is away from its occluding position.

20. The apparatus for aspirating a cytological sample as set forth in claim 19, wherein said means for creating a partial vacuum, and said means for moving and reciprocating said needle are electrically actuated and controlled.

21. The apparatus for aspirating a cytological sample as set forth in claim 19, wherein at least one of said means for creating a partial vacuum, and said means for moving and reciprocating said needle are pneumatically actuated and electrically controlled.

22. The apparatus for aspirating a cytological sample as set forth in claim 19, wherein at least one of said means for creating a partial vacuum, and said means for moving and reciprocating said needle are manually actuated and controlled.

23. The apparatus for aspirating a cytological sample as set forth in claim 19, and further comprising:
means for unoccluding said at least one peripheral opening by relative movement of said needle and said outer sleeve upon advancement of said needle and said outer sleeve a predetermined fixed distance towards said target area.

24. The apparatus set forth in claim 23, wherein said means for unoccluding said at least one peripheral opening includes a sheath surrounding at least a portion of said needle and cooperating with said outer sleeve.

* * * * *